(12) United States Patent
Berk

(10) Patent No.: US 8,999,944 B2
(45) Date of Patent: Apr. 7, 2015

(54) THIOREDOXIN INTERACTING PROTEIN (TXNIP) AS REGULATOR OF VASCULAR FUNCTION

(75) Inventor: Bradford C. Berk, Rochester, NY (US)

(73) Assignee: University of Rochester, Rochester, NY (US)

( * ) Notice: Subject to any disclaimer, the term of this patent is extended or adjusted under 35 U.S.C. 154(b) by 1623 days.

(21) Appl. No.: 11/814,442

(22) PCT Filed: Jan. 20, 2006

(86) PCT No.: PCT/US2006/001954
§ 371 (c)(1),
(2), (4) Date: Jun. 9, 2008

(87) PCT Pub. No.: WO2006/078853
PCT Pub. Date: Jul. 27, 2006

(65) Prior Publication Data
US 2011/0097317 A1    Apr. 28, 2011

Related U.S. Application Data

(60) Provisional application No. 60/645,380, filed on Jan. 20, 2005.

(51) Int. Cl.
| | |
|---|---|
| A61K 48/00 | (2006.01) |
| C07H 21/02 | (2006.01) |
| C07H 21/04 | (2006.01) |
| G01N 33/68 | (2006.01) |

(52) U.S. Cl.
CPC ........ *G01N 33/6893* (2013.01); *G01N 2500/02* (2013.01); *G01N 2500/10* (2013.01); *G01N 2800/32* (2013.01)

(58) Field of Classification Search
USPC .......................................................... 514/44
See application file for complete search history.

(56) References Cited

U.S. PATENT DOCUMENTS

| | | | |
|---|---|---|---|
| 6,540,996 B1 * | 4/2003 | Zwaal et al. | ............... 424/93.21 |
| 2005/0233992 A1 | 10/2005 | Itescu | |

FOREIGN PATENT DOCUMENTS

| | | |
|---|---|---|
| WO | 00/53769 A1 | 9/2000 |
| WO | 02/16416 A2 | 2/2002 |
| WO | 03/070188 A2 | 8/2003 |
| WO | 03/090512 A2 | 11/2003 |

OTHER PUBLICATIONS

Hammond et al. (Nature Reviews Genetics 2001, vol. 2:110-119).*
Nishiyama et al. "Redox Regulation by Thioredoxin and Thioredoxin-Binding Proteins," IUBMB Life 52:29-33 (2001).

(Continued)

*Primary Examiner* — Terra Cotta Gibbs
(74) *Attorney, Agent, or Firm* — LeClairRyan, a Professional Corporation

(57) ABSTRACT

The present invention relates to screening assays for the identification of agents that can modify the interaction of thioredoxin interacting protein (TXNEP) on thioredoxin (TRX)5 preferably by inhibiting TXNIP downregulation of TXR. The use of such compounds, including the disclosed siRNA and antibodies against TXNIP, is contemplated for therapeutic or prophylactic treatment of vascular disease conditions, particularly those associated with pro-inflammatory activity of the TNF-ASK1-JNK-p38 pathways.

9 Claims, 10 Drawing Sheets

(56) References Cited

OTHER PUBLICATIONS

Schulze et al., "Vitamin D3-Upregulated Protein-1 (VDUP-1) Regulates Redox-Dependent Vascular Smooth Muscle Cell Proliferation Through Interaction With Thioredoxin," Circ. Res. 91:689-695 (2002).

Extended European Search Report for corresponding EP application 09163278.6 (dated Sep. 8, 2009).

Yoshioka et al., "Thioredoxin-interaction Protein Controls Cardiac Hypertrophy Through Regulation of Thioredoxin Activity," AHA Circulation. 109:2581-2586 (2004).

Schulze et al., "Hyperglycemia Promotes Oxidative Stress through Inhibition of Thioredoxin Function by Thioredoxin-interacting Protein," Journal Biol. Chem. 279(29):30369-30374 (2004).

European Search Report for corresponding EP application 06718952.2 (dated Oct. 14, 2008).

Junn et al., "Vitamin D3 Up-Regulated Protein 1 Mediates Oxidative Stress Via Suppressing the Thioredoxin Function," J. of Immun. 164:6287-6295 (2000).

Yamawaki et al., "Thioredoxin A Key Regulator of Cardiovascular Homeostasis," Circ. Res. 93:1029-1033 (2003).

\* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: target for siRNA against human TXNIP

<400> SEQUENCE: 1
aagccgttag gatcctggct t                                              21

<210> SEQ ID NO 2
<211> LENGTH: 21
<212> TYPE: DNA
<213> ORGANISM: Artificial Sequence
<220> FEATURE:
<223> OTHER INFORMATION: control sequence

<400> SEQUENCE: 2
aattctccga acgtgtcacg t                                              21
```

THIOREDOXIN INTERACTING PROTEIN (TXNIP) AS REGULATOR OF VASCULAR FUNCTION

This application is a national stage application under 35 U.S.C. 371 of PCT/US2006/001954, filed Jan. 20, 2006, and claims the priority benefit of U.S. Provisional Patent Application Ser. No. 60/645,380, filed Jan. 20, 2005, which is hereby incorporated by reference in its entirety.

The present invention was made with government support under grants HL 064839, HL062826 and HL064858 awarded by the National Institutes of Health. The government has certain rights in the invention.

BACKGROUND OF THE INVENTION

Substantial evidence exists that physiologic fluid shear stress exerts atheroprotective effects in vivo, because atherosclerosis preferentially occurs in areas of disturbed flow or low shear stress, whereas regions with steady laminar flow and physiological shear stress are protected (Gimbrone et al., "Endothelial Dysfunction, Hemodynamic Forces, and Atherogenesis," *Ann NY Acad Sci* 902:230-239, Discussion 239-240 (2000); Traub et al., "Laminar Shear Stress: Mechanisms by Which Endothelial Cells Transduce an Atheroprotective Force," *Arterioscler Thromb Vasc Biol* 18:677-685 (1998)). Pathogenic features of atherosclerosis are oxidative stress and inflammation characterized by endothelial expression of vascular cell adhesion molecule-1 ("VCAM1") (Ross, R., "Atherosclerosis—An Inflammatory Disease," *N Eng J Med* 340:115-126 (1999)).

Apoptosis signal-regulating kinase 1 ("ASK1"), a mitogen-activated protein kinase kinase kinase (MAPKKK), plays essential roles in cytokine-related signaling and stress-induced apoptosis (Ichijo et al., "Induction of Apoptosis by ASK1, a Mammalian MAPKKK That Activates SAPK/JNK and p38 Signaling Pathways," *Science* 275:90-94 (1997)). Through genetic screening for ASK1-binding proteins, Saitoh et al. ("Mammalian Thioredoxin is a Direct Inhibitor of Apoptosis Signal-Regulating Kinase (ASK) 1," *EMBO J* 17:2596-2606 (1998)) found that thioredoxin ("TRX") bound directly to the N-terminus of ASK1 and inhibited ASK1 kinase activity as well as ASK1-dependent apoptosis. TRX is a ubiquitous thiol oxidoreductase that regulates cellular redox status. TRX can protect against oxidative stress-induced cell injury or inflammation directly via antioxidant effects and indirectly by protein-protein interaction with signaling molecules such as ASK1 (Yamawaki et al., "Thioredoxin: A Key Regulator of Cardiovascular Homeostasis," *Circ Res* 93:1029-1033 (2003)). TRX also exhibits growth-promoting effects presumably via an increased supply of reducing equivalents for DNA synthesis and activation of transcription factors that regulate cell growth. Thioredoxin interacting protein ("TXNIP," also termed VDUP1 for vitamin $D_3$-upregulated protein) was originally identified in HL-60 leukemia cells treated with 1,25-dihydroxyvitamin $D_3$ (Chen et al., "Isolation and Characterization of a Novel cDNA from HL-60 Cells Treated with 1,25-Dihydroxyvitamin D-3," *Biochim Biophys Acta* 1219:26-32 (1994)). Thereafter, Nishiyama et al. isolated TXNIP as a TRX-binding protein using a yeast two-hybrid system (Nishiyama et al., "Identification of Thioredoxin-Binding Protein-2/Vitamin D(3) Up-Regulated Protein 1 as a Negative Regulator of Thioredoxin Function and Expression," *J Biol Chem* 274:21645-21650 (1999)). Biochemical analysis showed that TXNIP inhibited TRX activity by interacting with the catalytic center of TRX (cysteines 32 and 35), suggesting that TXNIP is an endogenous inhibitor of TRX (Nishiyama et al., "Identification of Thioredoxin-Binding Protein-2/Vitamin D(3) Up-Regulated Protein 1 as a Negative Regulator of Thioredoxin Function and Expression," *J Biol Chem* 274:21645-21650 (1999); Junn et al., "Vitamin D3 Up-Regulated Protein 1 Mediates Oxidative Stress via Suppressing the Thioredoxin Function," *J Immunol* 164:6287-6295 (2000)).

There is accumulating evidence that TXNIP plays a pivotal role in cardiovascular disorders, functioning as a sensor for biomechanical and oxidative stress. Schulze et al. recently reported that hyperglycemia in vascular smooth muscle increased oxidative stress by inducing TXNIP and inhibiting the anti-oxidant function of TRX (Schulze et al., "Hyperglycemia Promotes Oxidative Stress Through Inhibition of Thioredoxin Function by Thioredoxin-Interacting Protein," *J Biol Chem* 279:30369-30374 (2004)). They also showed that diabetic animals exhibited increased vascular expression of TXNIP. Wang et al. recently demonstrated in cardiomyocytes that mechanical strain suppressed TXNIP expression followed by increases in TRX activity (Wang et al., "Vitamin D(3)-Up-Regulated Protein-1 is a Stress-Responsive Gene That Regulates Cardiomyocyte Viability Through Interaction with Thioredoxin," *J Biol Chem* 277:26496-26500 (2002). It has also been reported by Yoshioka et al. that TXNIP expression is decreased in pressure-overload cardiac hypertrophy followed by TRX-induced stimulation of cardiac cell growth (Yoshioka et al., "Thioredoxin-Interacting Protein Controls Cardiac Hypertrophy Through Regulation of Thioredoxin Activity," *Circulation* 109:2581-2586 (2004)).

It would be desirable, therefore, to identify whether inhibition of TXNIP in endothelial cells can have an atheroprotective effect via increased TRX activity, and decreased activity of JNK, p38, and VCAM1 expression. The present invention is directed to overcoming the above-identified deficiencies in the art.

SUMMARY OF THE INVENTION

A first aspect of the present invention relates to method of identifying a compound that inhibits the binding of thioredoxin interacting protein (TXNIP) to thioredoxin (TRX). This method includes the steps of: combining a TXNIP protein or polypeptide and a TRX protein or polypeptide, in the presence of a test compound, under conditions effective to allow the TXNIP protein or polypeptide to bind the TRX protein or polypeptide (i.e., in the absence of interference from the test compound); measuring the binding of the TRX protein or polypeptide by the TXNIP protein or polypeptide; and comparing the measured binding of the TRX protein or polypeptide by the TXNIP protein or polypeptide in the absence of the test compound with the measured binding of the TRX protein or polypeptide by the TXNIP protein or polypeptide in the presence of the test compound, wherein a decrease in binding indicates the test compound inhibits binding of the TRX protein or polypeptide by the TXNIP protein or polypeptide.

A second aspect of the present invention relates to a method of identifying the ability of a test compound to inhibit expression of TXNIP. This method includes the steps of: culturing one or more cells under conditions effective to upregulate TXNIP expression by the one or more cells; exposing the one or more cells to a test compound; and measuring TXNIP expression in the presence of the test compound, wherein a decrease in TXNIP expression, relative to expression in the absence of the test compound, indicates that the test compound inhibits TXNIP expression.

A third aspect of the present invention relates to a method of identifying the ability of a test compound to inhibit expression of TXNIP. This method includes the steps of: providing a cell transfected with a DNA construct that contains an isolated nucleic acid molecule encoding a TXNIP protein or polypeptide, a reporter gene, and 5' and 3' regulatory regions that allow transcription and translation of the nucleic acid molecule encoding the TXNIP protein or polypeptide and the reporter gene; incubating a test compound with the transfected cell; measuring the level of said reporter gene expressed in said cell; and comparing the level of expression of the reporter gene expressed in the transgenic cell in the absence of the test compound with the expression of the reporter gene in the presence of the test compound, wherein a decrease in reporter gene expression level indicates that the test compound inhibits TXNIP expression.

A fourth aspect of the present invention relates to a method of treating a vascular disease condition in a subject. This method includes the steps of: providing a compound that inhibits expression of thioredoxin interacting protein (TXNIP); and administering a therapeutically effective amount of the compound to a subject under conditions effective to inhibit expression of TXNIP in endothelial or vascular smooth muscle cells, thereby treating the vascular disease condition.

A fifth aspect of the present invention relates to a method of treating a vascular disease condition in a subject. This method includes the steps of: providing a compound that inhibits binding of thioredoxin interacting protein (TXNIP) to thioredoxin (TRX), and administering a therapeutically effective amount of the compound to a subject under conditions effective to inhibit binding of TXNIP to TRX in endothelial or vascular smooth muscle cells, thereby treating the vascular disease condition.

It is demonstrated in the accompanying examples that steady laminar flow inhibits VCAM1 expression by increasing anti-oxidant mechanisms and blocking inflammatory signaling events. The accompanying examples demonstrate that physiologic fluid shear stress decreases TXNIP expression and limits pro-inflammatory events mediated by the TNF-ASK1-JNK-p38 pathway (FIG. 10). In intact aortas, physiologic flow decreased TXNIP expression, and decreased TXNIP expression was associated with decreased TNF-mediated VCAM1 expression. The results are the first demonstration of the physiologic function of TXNIP in vascular endothelium. The accompanying examples further demonstrate that inhibition of TXNIP can replicate the effects of normal flow. The data support the evolving concept that TXNIP-TRX are key components of biomechanical signal transduction and establish TXNIP-TRX as novel regulators of TNF signaling and inflammation in the endothelium. By inhibiting TXNIP expression or binding to TRX, the pro-inflammatory events mediated by the TNF-ASK1-JNK-p38 pathway can be controlled.

BRIEF DESCRIPTION OF THE DRAWINGS

As illustrated in FIG. 1C, TXNIP expression is shown as fold change relative to low flow. **: P<0.01 from low flow.

FIG. 2A shows TRX activity as determined by the insulin-reducing assay. Results are shown as fold change relative to low flow (n=4, *P<0.05) from low flow. FIG. 2B shows that TRX expression was unchanged in low and normal flow (n=5).

FIG. 3A shows TXNIP and TRX expression levels as determined by immunoblotting (n=4). Equal protein loading was confirmed with actin antibody. TXNIP expression is shown as fold change relative to low flow. The ratio in normal flow differed significantly from low flow (n=4, P<0.05). FIG. 3B shows TRX activity as determined by the insulin reducing assay. Results are shown as fold change relative to low flow (n=4, *P<0.05) from low flow.

FIG. 4A shows TXNIP expression as determined by immunoblotting from 4-6 independent experiments. Equal protein loading was confirmed with eNOS antibody. FIG. 4B shows TXNIP expression as fold change relative to no siRNA.**: P<0.01 from control siRNA.

DETAILED DESCRIPTION OF THE INVENTION

Figure 1:
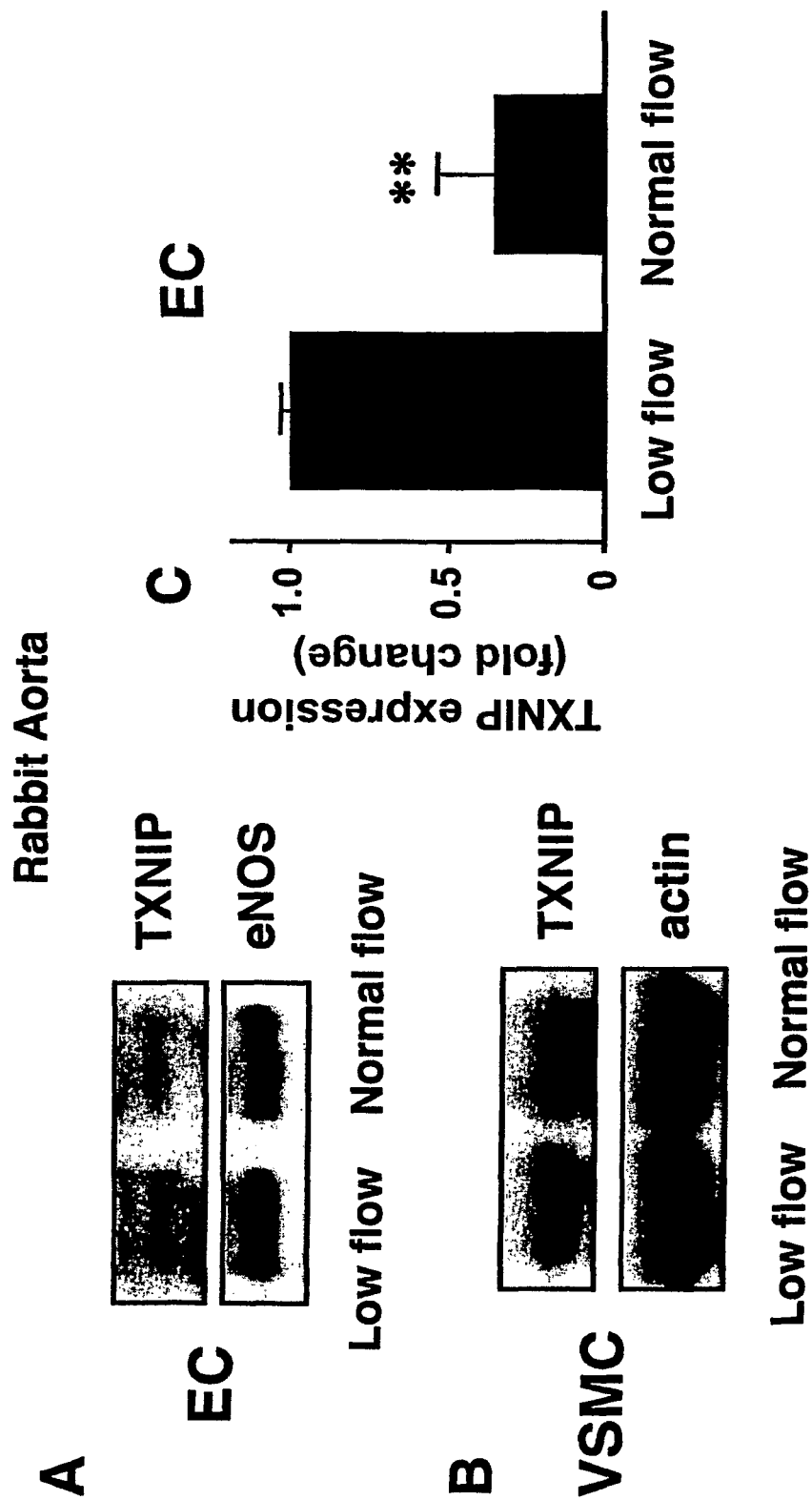
FIGS. 1A-C illustrate that normal flow down-regulates TXNIP expression in endothelial cells ("EC"). After rabbit aortas were exposed to low flow (0.4 dyn/cm$^2$) or normal flow (12 dyn/cm$^2$) for 24 h, EC (FIG. 1A) and vascular smooth muscle cells ("VSMC", FIG. 1B) proteins were selectively purified, and immunoblotting was performed (n=4-5). Equal protein loading was confirmed with eNOS or actin antibody.

According to one aspect of the present invention, several screening assays (i.e., methods) are provided for identifying one or more agents (i.e., test compounds, proteins, peptides, peptidomimetics, small molecules, or other drugs) that can modify expression of thioredoxin interacting protein (TXNIP) or its binding of TXNIP to thioredoxin (TRX). Preferably, such assays are used to measure inhibition of TXNIP expression or inhibition of its binding to TRX, although it is contemplated that such assays can be used to measure enhancement of TXNIP expression or enhancing binding activity of TXNIP to TRX.

As used herein, "inhibit" is intended to mean any measurement of a decrease relative to a control, whereas "enhance" is intended to mean any measurement of an increase relative to a control.

Thus, inhibiting expression of TXNIP means any reduction of TXNIP expression relative to TXNIP expression in a corresponding control. With regard to such inhibition, it is preferable that TXNIP expression can be inhibited by at least about 50%, more preferably at least about 75% up to about 90%. It is expected that TXNIP expression can be substantially precluded in some instances, i.e., having expression reduced by at least about 95%. Likewise, inhibition of TXNIP binding to TRX means any reduction in the binding of TRX, relative to TRX binding in a corresponding control. Preferably, TXNIP binding to TRX can be inhibited by at least about 50%, more preferably at least about 75% up to about 90%. It is expected that TXNIP binding to TRX can be substantially precluded or entirely blocked in some instances, i.e., having binding reduced by at least about 95%.

In another aspect, the present invention provides a method for identifying a test compound that binds to or modulates the binding activity of a TXNIP protein. In general, such methods entail measuring a biological activity of a TXNIP protein in the presence and absence of a test compound and identifying those compounds which alter the activity of the TXNIP protein.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, monoclonal or polyclonal antibodies, non-peptide oligomer or small molecule libraries of compounds (Lam, *Anticancer Drug Des.* 12:145 (1997), which is hereby incorporated by reference in its entirety). Examples of methods for the synthesis of molecular libraries can be found in the art, for example in: DeWitt et al., *Proc. Natl. Acad. Sci. USA* 90:6909 (1993); Erb et al., *Proc. Natl. Acad. Sci. USA* 91:11422 (1994); Zuckermann et al., *J. Med. Chem.* 37:2678; (1994); Cho et al., *Science* 261:1303 (1993); Carrell et al., Angew. *Chem. Int. Ed. Engl.* 33:2059 (1994); Carell et al., Angew. *Chem. Int. Ed. Engl.* 33:2061 (1994); and Gallop et al., *J. Med. Chem.* 37:1233 (1994), each of which is hereby incorporated by reference in its entirety.

Libraries of compounds may be presented in solution (e.g., Houghten, *Bio/Techniques* 13:412-421 (1992), which is hereby incorporated by reference in its entirety), or on beads (Lam, *Nature* 354:82-84 (1991), which is hereby incorporated by reference in its entirety), chips (Fodor, *Nature* 364: 555-556 (1993), which is hereby incorporated by reference in its entirety), bacteria (U.S. Pat. No. 5,223,409, which is hereby incorporated by reference in its entirety), spores (U.S. Pat. Nos. 5,571,698; 5,403,484; and 5,223,409, each of which is hereby incorporated by reference in its entirety), plasmids (Cull et al., *Proc. Natl. Acad. Sci. USA* 89:1865-1869 (1992) which is hereby incorporated by reference in its entirety), or on phage (Scott and Smith, Science 249:386-390 (1990); Devlin, *Science* 249:404-406(1990); Cwirla et al., *Proc. Natl. Acad. Sci. USA* 87:6378-6382 (1990); Felici, *J. Mol. Biol.* 222:301-310 (1991), each of which is hereby incorporated by reference in its entirety).

These screening assays can be performed in the presence of cells or in a cell-free format. For cell-based assays, the cells are preferably mammalian cells (e.g., human, non-human primate, porcine, bovine, rat, mouse, etc.), most preferably mammalian endothelial cells.

In one embodiment, the assay is directed to the identification of a compound that inhibits the binding of TXNIP to TRX. This method involves combining a TXNIP protein or polypeptide (i.e., biologically active portion thereof) and a TRX protein or polypeptide (i.e., biologically active portion thereof), in the presence of a test compound, under conditions effective to allow the TXNIP protein or polypeptide to bind the TRX protein or polypeptide; and then measuring the binding of the TRX protein or polypeptide by the TXNIP protein or polypeptide. Upon comparing the measured binding of the TRX protein or polypeptide by the TXNIP protein or polypeptide in the absence of the test compound with the measured binding of the TRX protein or polypeptide by the TXNIP protein or polypeptide in the presence of the test compound, it is possible to assess the efficacy of the test compound. Where a decrease in binding occurs, the test compound inhibited binding of the TRX protein or polypeptide by the TXNIP protein or polypeptide.

Detection of binding can be achieved through any suitable procedure that is known in the art or hereafter developed. Exemplary procedures for use in a cell-free format include, without limitation, a competitive binding assay, direct measurement, or detecting changes in the activity of TRX (an indirect measure of TXNIP binding to TRX). As for the binding that is to be detected, either binding of the test compound to TXNIP or binding of the test compound to TRX can be measured. Exemplary procedures for use in a cell-based assay include, without limitation, detection of a cellular secondary messenger such as catalytic/enzymatic activity of TRX (see FIG. 10), detection of a reporter protein, or measurement of a cellular response (cell survival, cell differentiation, cell proliferation).

In certain cell-free assays, it may be desirable to immobilize either TXNIP or its target molecule, including but not limited to TRX, to facilitate separation of complexed from uncomplexed forms of one or both of the proteins, as well as to accommodate automation of the assay. Binding of a test compound to TXNIP, or interaction of TXNIP with a target molecule in the presence and absence of a candidate test compound, can be accomplished in any vessel suitable for containing the reactants. Examples of such vessels include, without limitation, microtiter plates, test tubes, and microcentrifuge tubes.

In one approach, a fusion protein can be provided which adds a domain that allows one or both of the proteins to be bound to a matrix. For example, glutathione-S-transferase/TXNIP fusion proteins or glutathione-S-transferase/TRX fusion proteins can be adsorbed onto glutathione sepharose beads (Sigma Chemical; St. Louis, Mo.) or glutathione derivatized microtiter plates, which are then combined with the test compound or the test compound and either the non-adsorbed TRX or TXNIP, and the mixture incubated under conditions conducive to complex formation (e.g., at physiological conditions for salt and pH). Following incubation, the beads or microtiter plate wells are washed to remove any unbound components, the matrix immobilized in the case of beads, and complex determined either directly or indirectly, for example, as described above. Alternatively, the complexes can be dissociated from the matrix, and the level of TXNIP binding or activity determined using standard techniques.

Other techniques for immobilizing proteins on matrices can also be used in the screening assays of the invention. For example, either TXNIP or TRX can be immobilized utilizing conjugation of biotin and streptavidin. Biotinylated TXNIP or TRX can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with TXNIP or TRX, but which do not interfere with their binding, can be derivatized to the wells of the plate, and unbound TXNIP or TRX trapped in the wells by antibody conjugation. Methods for detecting such complexes, in addition to those described above for the GST-immobilized complexes, include immunodetection of complexes using antibodies reactive with the TXNIP or TRX, as well as enzyme-linked assays which rely on detecting an enzymatic activity associated with the TXNIP or TRX.

In another embodiment, the assay can be used to identify the ability of a test compound to inhibit expression of TXNIP. This method involves culturing one or more cells under conditions effective to upregulate TXNIP expression by the one or more cells. After exposing the one or more cells to a test compound, TXNIP expression levels can be measured in the presence of the test compound. A decrease in TXNIP expression, relative to expression in the absence of the test compound, indicates that the test compound inhibits TXNIP expression. An increase in TXNIP expression, relative to expression in the absence of the test compound, indicates that the test compound enhances TXNIP expression.

Exemplary conditions that can upregulate TXNIP expression include, without limitation, (i) culturing the one or more cells in an apparatus that provides culture medium flowing past the one or more cells at a rate that is sufficient to upregulate TXNIP expression; (ii) treating the cells with 1,25-dihydroxyvitamin $D_3$ (Chen et al., "Isolation and Characterization of a Novel cDNA from HL-60 Cells Treated with 1,25-Dihydroxyvitamin D-3," *Biochem Biophys Acta* 1219:26-32 (1994), which is hereby incorporated by reference in its entirety); and (iii) exposing the cells to a medium that is high in glucose (i.e., consistent with replicating a hyperglycemic serum) (Schulze et al., "Hyperglycemia Promotes Oxidation Stress Through Inhibition of Thiroredoxin Function by Thioredoxin-Interacting Protein," *J. Biol. Chem.* 279:30369-30374 (2004), which is hereby incorporated by reference in its entirety). Other compounds or conditions that can upregulate TXNIP expression can also be used.

This cell-based assay for TXNIP expression is preferably carried out in an apparatus that can produce a flow rate sufficient to induce TXNIP expression. Basically, this is a low-shear force environment, where the flow rate is less than the normal range encountered in healthy vasculature (where TXNIP expression is largely suppressed). By way of example, flow rates of less than about 5 $dyn/cm^2$, more preferably less than about 2 $dyn/cm^2$, most preferably less than about 1 $dyn/cm^2$ (e.g., about 0.4 $dyn/cm^2$), should be suitable to induce TXNIP expression. Exemplary apparatuses include, without limitation, a cone and plate viscometer, a parallel-plate flow apparatus, and a vessel organ culture.

Detection of TXNIP expression levels can be carried out either by measuring TXNIP mRNA transcripts or by measurement of the protein itself. Thus, any suitable mRNA detection procedure can be employed, such as RT-PCR and/or Northern blotting. Likewise, any suitable immunoassay can be employed for detecting TXNIP, such as enzyme-linked immunoabsorbent assay, radioimmunoassay, gel diffusion precipitin reaction assay, immunodiffusion assay, agglutination assay, fluorescent immunoassay, protein A immunoassay, or immunoelectrophoresis assay.

In yet another embodiment, the TXNIP proteins can be used as "bait" and the TRX proteins as "prey" in a two-hybrid assay or three hybrid assay (see, e.g., U.S. Pat. No. 5,283,317; Zervos et al., *Cell* 72:223-232 (1993); Madura et al., *J. Biol. Chem.* 268:12046-12054 (1993); Bartel et al., *Bio/Techniques* 14:920-924 (1993); Iwabuchi et al., *Oncogene* 8:1693-1696(1993); PCT Publication No. WO 94/10300, each of which is hereby incorporated by reference in its entirety).

The two-hybrid system is based on the modular nature of most transcription factors, which consist of separable DNA-binding and activation domains. Briefly, the assay utilizes two different DNA constructs. In one construct, the gene that codes for TXNIP is fused to a gene encoding the DNA binding domain of a known transcription factor (e.g., GAL-4). In the other construct, a DNA sequence that encodes for TRX is fused to a gene that codes for the activation domain of the known transcription factor. If the "bait" and the "prey" proteins are able to interact, in vivo, forming a TXNIP-TRX complex, the DNA-binding and activation domains of the transcription factor are brought into close proximity. This proximity allows transcription of a reporter gene (e.g., LacZ), which is operably linked to a transcriptional regulatory site responsive to the transcription factor.

If the two-hybrid or three-hybrid systems can be carried out in the presence of a test compound, it is possible to differentiate those test compounds that inhibit expression of the reporter gene (which block TXNIP-TRX interaction) or enhance expression of the reporter gene (which enhance TXNIP-TRX interaction), or have no effect whatsoever. Expression of the reporter gene can be detected using appropriate detection procedures.

According to another embodiment, the screening assay is a cell-based assay that utilizes a cell transfected with a DNA construct that includes an isolated nucleic acid molecule encoding TXNIP, a reporter gene, and 5' and 3' regulatory regions that allow transcription and translation of the nucleic acid molecule encoding the TXNIP protein or polypeptide and the reporter gene. The method also involves incubating a test compound with the transfected cell, measuring the level of the reporter gene expressed in the cell; and comparing the level of expression of the reporter gene expressed in the transgenic cell in the absence of the test compound with the expression of the reporter gene in the presence of the test compound. A decrease in reporter gene expression level indicates that the test compound is able to inhibit TXNIP expression.

In this aspect, a DNA construct is prepared using conventional recombinant technology. Generally, this involves inserting the nucleic acid molecule into an expression system to which the molecule is heterologous (i.e., not normally present). The heterologous nucleic acid molecule is inserted into the expression system or vector in proper sense (5'→3') orientation relative to the promoter region, and in correct reading frame. Alternatively, the nucleic acid may be inserted in the "antisense" orientation, (3'→5') relative to the promoter (5' regulatory) region. The vector contains the necessary elements for the transcription and translation of the inserted protein-coding sequences in a desired host cell or organism.

In any aspect of the present invention in which down-regulation of TXNIP expression is desired (see prophylactic or therapeutic treatments, infra), the method may involve an RNA-based form of gene-silencing known as RNA-interference (RNAi). Numerous reports have been published on critical advances in the understanding of the biochemistry and genetics of both gene silencing and RNAi (Matzke et al., "RNA-Based Silencing Strategies in Plants," *Curr. Opin. Genet. Dev.* 11(2):221-227 (2001), which is hereby incorporated by reference in its entirety). In RNAi, the introduction of double stranded RNA (dsRNA, or iRNA, for interfering RNA) into animal or plant cells leads to the destruction of the endogenous, homologous mRNA, phenocopying a null mutant for that specific gene. In both post-transcriptional gene silencing and RNAi, the dsRNA is processed to short interfering molecules of 21-, 22- or 23-nucleotide RNAs (siRNA) by a putative RNAaseIII-like enzyme (Tuschl T., "RNA Interference and Small Interfering RNAs," *Chembiochem* 2:239-245 (2001); Zamore et al., "RNAi: Double Stranded RNA Directs the ATP-Dependent Cleavage of mRNA at 21 to 23 Nucleotide Intervals," *Cell* 101:25-3, (2000), each of which is hereby incorporated by reference in its entirety). The endogenously generated siRNAs mediate and direct the specific degradation of the target mRNA. In the case of RNAi, the cleavage site in the MRNA molecule targeted for degradation is located near the center of the region covered by the siRNA (Elbashir et al., "RNA Interference is Mediated by 21- and 22-Nucleotide RNAs," *Gene Dev.* 15(2): 188-200 (2001), which is hereby incorporated by reference in its entirety). The dsRNA for the nucleic acid molecule of the present invention can be generated by transcription in vivo, which involves modifying the nucleic acid molecule encoding TXNIP for the production of dsRNA, inserting the modified nucleic acid molecule into a suitable expression vector having the appropriate 5' and 3' regulatory nucleotide sequences operably linked for transcription and translation, and introducing the expression vector having the modified nucleic acid molecule into a suitable host cell or subject. Alternatively, complementary sense and antisense RNAs derived from a substantial portion of the coding region of the TXNIP nucleic acid molecule are synthesized in vitro (Fire et al., "Specific Interference by Ingested dsRNA," *Nature* 391: 806-811 (1998); Montgomery et al, "RNA as a Target of Double-Stranded RNA-Mediated Genetic Interference in *Caenorhabditis elegans*," *Proc. Natl Acad Sci USA* 95:15502-15507; Tabara et al., "RNAi in *C. elegans*: Soaking in the Genome Sequence," *Science* 282:430-431 (1998), each of which is hereby incorporated by reference in its entirety). The resulting sense and antisense RNAs are annealed in an injection buffer, and dsRNA is administered to the subject using any method of administration described herein, infra.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein or RNA-encoding sequences of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/- or KS+/- (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

Mammalian cells can also be used for any cell-based assays or for production of therapeutic nucleic acids. The mammalian cells can be isolated primary endothelial cells, or they can be commercially available mammalian cell lines. Suitable expression vectors for directing expression in mammalian cells generally include a promoter, as well as other transcription and translation control sequences known in the art. Common promoters operable in mammalian cells include, without limitation, SV40, MMTV, metallothionein-1, adenovirus Ela, CMV, immediate early, immunoglobulin heavy chain promoter and enhancer, and RSV-LTR.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The nucleic acid molecule(s) of the present invention, a promoter molecule (i.e., 5' regulatory region) of choice, a suitable 3' regulatory region, and if desired, a reporter gene, are incorporated into a vector-expression system of choice to prepare the nucleic acid construct of present invention using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

In one aspect of the present invention, a reporter gene is included in the DNA construct, and is operably arranged between an isolated nucleic acid molecule encoding a TXNIP protein or polypeptide, and appropriate 5' and 3' regulatory regions so that the expression of the TXNIP protein or polypeptide directly correlates to the expression of the reporter gene. Suitable reporter genes for this aspect include GFP, some κ-LacZ, β-gal, and any others known in the art. This construct is suitable for use in one or more of the screening methods described herein.

In one aspect of the present invention, a nucleic acid molecule encoding a TXNIP protein is inserted into a vector in the sense (i.e., 5'→3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct of the present invention. In another aspect, the nucleic acid molecule may be inserted into the expression system or vector in the antisense (i.e., 3'→5') orientation.

Once the isolated nucleic acid molecule encoding the TXNIP protein or polypeptide has been cloned into an expression system, it is ready to be incorporated into a host cell. Recombinant molecules can be introduced into cells via transformation, particularly transduction, conjugation, lipofection, protoplast fusion, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, mammalian cells, insect cells, and the like.

Methods of Treatment

The present invention further pertains to novel agents identified by the above-described screening assays and uses thereof for treatments as described below. Both prophylactic and therapeutic methods of treating a subject at risk of (or susceptible to) a disorder or disease condition, or having a disorder or disease condition associated with TXNIP expression or activity, are contemplated. The subject to whom the agent or composition is to be administered can be any mammal, preferably a rodent, dog, cat, cow, horse, sheep, pig, llama, alpaca, non-human primate, or human.

Disorders or disease conditions associated with undesirable TXNIP expression or activity include, without limitation, both chronic and acute vascular diseases, such as atherosclerosis, stroke, ischemia, myocardial infarction, coronary artery disease, cardio-vascular disease, hypertension, peripheral vascular disease, heart failure, diabetes, and sepsis.

The active agents (or compositions) can be administered in any manner that is effective to deliver the agent to affected endothelial or vascular smooth muscle cells (where TXNIP expression or activity is intended to be modified). This can be accomplished either via systemic administration to the subject or via targeted administration to affected endothelial or vascular smooth muscle cells, i.e., endothelial or vascular smooth muscle cells that are associated with disease-affected vasculature. Exemplary routes of administration include, without limitation, orally, by inhalation, by intranasal instillation, topically, transdermally, parenterally, subcutaneously, intravenous injection, intra-arterial injection (such as via the pulmonary artery), intramuscular injection, intrapleural instillation, intraperitoneally injection, intraventricularly, intralesionally, by application to mucous membranes, or implantation of a sustained release vehicle adjacent to the affected endothelial or vascular smooth muscle cells. Of these, intravenous, intra-arterial, and intraventricular, and inhalation routes of administration are preferred.

The administration of the therapeutic agent can be carried out as frequently as required and for a duration that is suitable to provide effective treatment for the disease conditions being treated. For example, administration of the therapeutic agent can be carried out with a single sustained-release dosage formulation or with multiple daily doses of the therapeutic agent. The amount to be administered will, of course, vary depending upon the treatment regimen.

Typically, the therapeutic agent will be administered to a mammal as a pharmaceutical composition that includes the therapeutic agent and any pharmaceutically acceptable suitable adjuvants, carriers, excipients, or stabilizers, and can be in solid or liquid form such as, tablets, capsules, powders, solutions, suspensions, or emulsions. The compositions preferably contain from about 0.01 to 99 weight percent, more preferably from about 2 to 60 percent, of therapeutic agent together with the adjuvants, carriers and/or excipients. The amount of active compound in such therapeutically useful compositions is such that a suitable dosage unit will be obtained. Preferred compositions according to the present invention are prepared so that a single dosage unit contains between about 1 mg and 1000 mg of the therapeutic agent.

In one aspect, the invention provides a method for preventing in a subject, a disease or condition associated with an TXNIP expression or activity, by administering to the subject an effective amount of an agent that modulates TXNIP expression or at least one TXNIP activity (e.g., binding of TRX). Subjects at risk for a disease which is caused or contributed to by aberrant TXNIP expression or activity can be identified by, for example, any or a combination of diagnostic or prognostic assays that are known in the art. Prophylactic administration of an agent can occur prior to the manifestation of symptoms characteristic of the TXNIP aberrancy, such that a disease or disorder is prevented or, alternatively, delayed in its progression. Depending on the type of TXNIP aberrancy, for example, a TXNIP agonist or TXNIP antagonist agent can be used for treating the subject. The appropriate agent can be determined based on screening assays described herein.

According to one embodiment, an inhibitor of TXNIP expression or an inhibitor of TXNIP binding to TRX, or a combination thereof, can be administered to a patient for purposes of preventing or delaying onset of symptoms associated with chronic vascular diseases of the type described above.

Another aspect of the invention pertains to methods of modulating TXNIP expression or TXNIP binding activity (i.e., binding to TRX) for therapeutic purposes. The modulatory method of the invention involves contacting a cell with an agent that modulates TXNIP expression or activity. An agent that modulates TXNIP protein activity can be any agent as described herein, such as a nucleic acid or a protein (e.g., an anti-TXNIP antibody) as described above, a naturally-occurring cognate ligand of TXNIP, a peptide, a peptidomimetic, or other small molecule.

According to one approach, an agent that inhibits expression of thioredoxin interacting protein (TXNIP) can be administered to a subject in a therapeutically effective amount and in a manner suitable to inhibit expression of TXNIP in endothelial or vascular smooth muscle cells, thereby treating the vascular disease condition. One example of such an agent is siRNA targeted to the TXNIP nucleotide sequence of SEQ ID NO: 1, which interferes with translation of the TXNIP protein. Other siRNA for TXNIP can also be selected using the online GenScript Corp. service, Promega Corp. service, or Ambion Inc. service.

The siRNA can be administered to the subject systemically as described herein or otherwise known in the art. Systemic administration can include those described above, but preferably intravenous, intraarterial, subcutaneous, intramuscular, catheterization, or nasopharangeal as is generally known in the art. Alternatively, the siNA can be administered to the subject locally or to local tissues as described herein or otherwise known in the art. Local administration can include, for example, catheterization, implantation, direct injection, dermal/transdermal application, stenting, ear/eye drops, or portal vein administration to relevant tissues, or any other local administration technique, method or procedure, as is generally known in the art.

Delivery of siRNA is preferably administered alone or as a component of a composition. Suitable compositions include the siRNA formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see, e.g., Ogris et al., *AAPA Pharm Sci* 3:1-11 (2001); Furgeson et al., *Bioconjugate Chem.*, 14:840-847 (2003); Kunath et al., *Pharmaceutical Res*, 19: 810-817 (2002); Choi et al., *Bull. Korean Chem. Soc.* 22:46-52 (2001); Bettinger et al., *Bioconjugate Chem.* 10:558-561 (1999); Peterson et al., *Bioconjugate Chem.* 13:845-854 (2002); Erbacher et al., *J. Gene Medicine Preprint* 1:1-18 (1999); Godbey et al., *Proc Natl Acad Sci USA* 96:5177-5181 (1999); Godbey et al., *J Controlled Release* 60:149-160 (1999); Diebold et al., *J Biol Chem* 274: 19087-19094 (1999); Thomas and Klibanov, *Proc Natl Acad Sci USA* 99:14640-14645 (2002); and U.S. Pat. No. 6,586, 524 to Sagara, each of which is hereby incorporated by reference in its entirety.

The siNA molecule can also be present in the form of a bioconjugate, for example a nucleic acid conjugate as described in U.S. Pat. No. 6,528,631, U.S. Pat. No. 6,335,434, U.S. Pat. No. 6,235,886, U.S. Pat. No. 6,153,737, U.S. Pat. No. 5,214,136, or U.S. Pat. No. 5,138,045, each of which is hereby incorporated by reference in its entirety.

The siRNA, or any composition or bioconjugate containing the same, can be administered via a liposomal delivery mechanism. Basically, this involves providing a liposome which includes the siRNA to be delivered, and then contacting the target cell with the liposome under conditions effective for delivery of the siRNA into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g. *Proc. Natl. Acad. Sci. USA* 84:7851 (1987); *Biochemistry* 28:908 (1989), each of which is hereby incorporated by reference in its entirety). When liposomes are endocytosed by a target cell, for example, they can be routed to acidic endosomes which will destabilize the liposome and result in drug release.

The liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference.

These liposomes can be produced such that they contain, in addition to siRNA, other therapeutic agents, such as anti-inflammatory agents, which would then be released at the target site (e.g., Wolff et al., *Biochem. et Biophys. Acta* 802: 259 (1984), which is hereby incorporated by reference in its entirety).

As an alternative to non-infective delivery of the inhibitory RNA as described above, naked DNA or infective transformation vectors can be used for delivery, whereby the naked DNA or infective transformation vector contains a recombinant gene that encodes the inhibitory RNA capable of inhibiting expression of TXNIP. The inhibitory RNA molecule is then expressed in the transformed cell.

The recombinant gene includes, operatively coupled to one another, an upstream promoter operable in mammalian cells and optionally other suitable regulatory elements (i.e., enhancer or inducer elements), a coding sequence that encodes the therapeutic nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in endothelial cells, such as the Tie2 promoter (Minami et al., "Ets Motifs are Necessary for Endothelial Cell-specific Expression of a 723-bp Tie-2 Promoter/Enhancer in hprt targeted transgenic mice," *Arterioscl. Thromb. Vasc. Biol.* 23(11):2041-2047 (2003), which is hereby incorporated by reference in its entirety), or in vascular smooth muscle cells, such as SM22 (Ribault et al., "Chimeric Smooth Muscle-Specific Enhancer/Promoters: Valuable Tools for Adenovirus-mediated Cardiovascular Gene Therapy," *Circulation Res.* 88(5):468-475 (2001), which is hereby incorporated by reference in its entirety). Tissue specific promoters can also be made inducible/repressible using, e.g., a TetO response element. Other inducible elements can also be used. Known recombinant techniques can be utilized to prepare the recombinant gene, transfer it into the expression vector (if used), and administer the vector or naked DNA to a patient. Exemplary procedures are described in Sambrook et al., *Molecular Cloning: A Laboratory Manual*, Second Edition, Cold Spring Harbor Press, NY (1989), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., *Science* 258:1485-1488 (1992); Walsh et al., *Proc. Natl Acad. Sci. USA* 89:7257-7261 (1992); Walsh et al., *J. Clin. Invest.* 94:1440-1448 (1994); Flotte et al., *J. Biol. Chem.* 268:3781-3790 (1993); Ponnazhagan et al., *J. Exp. Med.* 179: 733-738 (1994); Miller et al., *Proc. Nat'l Acad. Sci. USA* 91:10183-10187 (1994); Einerhand et al., *Gene Ther.* 2:336-343 (1995); Luo et al., *Exp. Hematol.* 23:1261-1267 (1995); and Zhou et al., *Gene Ther.* 3:223-229 (1996), each of which is hereby incorporated by reference in its entirety. In vivo use of these vehicles is described in Flotte et al., *Proc. Nat'l Acad. Sci. USA* 90:10613-10617 (1993); and Kaplitt et al., *Nature Genet.* 8:148-153 (1994), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler et al., which is hereby incorporated by reference in its entirety. Lentivirus vectors can also be utilized, including those described in U.S. Pat. No. 6,790,657 to Arya, and U.S. Patent Application Nos. 20040170962 to Kafri et al. and 20040147026 to Arya, each of which is hereby incorporated by reference in its entirety.

According to another approach, an agent that inhibits binding of TXNIP to TRX can be administered to a subject in a therapeutically effective amount and in a manner suitable to inhibit this activity of TXNIP in endothelial or vascular smooth muscle cells, thereby treating the vascular disease condition. One example of such an agent is an anti-TXNIP antibody or functional fragment thereof.

Suitable anti-TXNIP antibodies can polyclonal antibodies or monoclonal antibodies, although monoclonal are preferred. The antibody may also be isoform-specific. The monoclonal antibody or binding fragment thereof can be in the form of Fab fragments, F(ab)2 fragments, Fab' fragments, F(ab')2 fragments, Fd fragments, Fd' fragments or Fv fragments. Domain antibodies (dAbs) (see, e.g., Holt et al., *Trends in Biotechnology* 21:484-490 (2003), which is hereby incorporated by reference in its entirety) are also suitable for the methods of the present invention.

Various methods of producing antibodies with a known antigen are well-known to those ordinarily skilled in the art (Harlow and Lane, *Antibodies: A Laboratory Manual*, Cold Spring Harbor Laboratory Press, Cold Spring Harbor, N.Y. (1988), which is hereby incorporated by reference in its entirety). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

As noted above, the antibodies or fragments thereof are intended to be administered in vivo. Antibodies can be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in, e.g., Morrison et al., *Proc. Natl. Acad. Sci. USA* 81:6851-6855 (1984); Neuberger et al., *Nature* 312:604-608 (1984); Takeda et al., *Nature* 314:452-454 (1985), each of which is hereby incorporated by reference in its entirety). For human therapeutic purposes, humanized antibodies or fragments can be used.

Further, single chain antibodies are also suitable for the present invention (e.g., U.S. Pat. Nos. 5,476,786 and 5,132,405 to Huston; Huston et al., *Proc. Natl. Acad. Sci. USA,* 85:5879-5883 (1988); U.S. Pat. No. 4,946,778 to Ladner et al.; Bird, *Science* 242:423-426 (1988); Ward et al., *Nature* 334:544-546 (1989), each of which is hereby incorporated by reference in its entirety). Single chain antibodies are formed by linking the heavy and light immunoglobulin chain fragments of the Fv region via an amino acid bridge, resulting in a single chain polypeptide. Univalent antibodies are also embraced by the present invention.

Many routes of delivery are known to the skilled artisan for delivery of anti-target antibodies. For example, direct injection may be suitable for delivering the antibody to the site of interest. It is also possible to utilize liposomes with antibodies in their membranes to specifically deliver the liposome to the area where TXNIP expression or function is to be inhibited (i.e., in endothelial cells within an affected area). These liposomes can be produced such that they contain, in addition to monoclonal antibody, other therapeutic agents, such as those described above, which would then be released at the target site.

In addition to inhibiting TXNIP expression or binding of TRX, it is also contemplated that TRX levels can be enhanced. This can be accomplished by any suitable means. For example, according to one approach TRX protein or polypeptide can be delivered to affected endothelial or vascular smooth muscle cells (i.e., recombinantly produced and then delivered) via standard protein delivery systems such as conjugation or liposomes. According to another approach, the TRX protein or polypeptide can be constitutively or inducibly expressed in vivo via gene therapy (i.e., transformation of the affected endothelial or vascular smooth muscle cells with a recombinant vector containing a gene encoding TRX). These approaches can be performed alone or in combination with the above-identified forms of TXNIP inhibition.

It is also contemplated that stimulation of TXNIP activity may be desirable in situations in which TXNIP is abnormally downregulated and/or in which increased TXNIP activity is likely to have a beneficial effect. Compounds, identified in the screening assays described herein, that enhance TXNIP expression or binding to TRX, or otherwise inhibit TRX activity (e.g., such as an anti-TRX antibody or effective fragment thereof) can be administered in the manner described above.

EXAMPLES

The following examples are provided to illustrate embodiments of the present invention but are by no means intended to limit its scope.

Materials and Methods

Antibodies and Reagents:

VCAM1, ERK½, p38, eNOS, actin, and IκB-α (Santa Cruz); phospho-ERK½, -p38, JNK2, and ASK1 (Cell Signaling); phospho-JNK (Promega); and human TRX1 (American Diagnostica Inc.). Rabbit polyclonal antibody against mouse TXNIP and mouse monoclonal antibody against human TXNIP were developed as previously described (Wang et al., "Vitamin D(3)-Up-Regulated Protein-1 is a Stress-Responsive Gene That Regulates Cardiomyocyte Viability Through Interaction with Thioredoxin," *J Biol Chem* 277:26496-26500 (2002); Schulze et al., "Vitamin D3-Upregulated Protein-1 (VDUP-1) Regulates Redox-Dependent Vascular Smooth Muscle Cell Proliferation Through Interaction With Thioredoxin," *Circ Res* 91:689-695 (2002), each of which is hereby incorporated by reference in its entirety). TNF-α (Roche); JNK inhibitor SP600125, p38 inhibitor SB203580, and ERK inhibitor PD98059 (Calbiochem).

Cell Culture, siRNA Oligoizucleotide Treatment, and Plasmid Transfection:

Human umbilical vein EC ("HUVEC") were purchased from Cascade Biologics and cultured in Medium 200 supplemented with low serum growth supplement (LSGS, Cascade Biologics). Cells at passages 3-5 were used for experiments.

To knockdown TXNIP, HUVEC were treated with small interference RNA (siRNA) against human TXNIP coding region. The target sequences were: 5'-AAG CCG TTA GGA TCC TGG CTT (SEQ ID NO: 1) for human TXNIP and 5'-AAT TCT CCG AAC GTG TCA CGT-3' (SEQ ID NO: 2) for control non-silencing siRNA, respectively (Qiagen-Xeragon). HUVEC at >90% confluence in 60-mm dishes were used for transfection. For each dish, Lipofectamine 2000 (Invitrogen) was mixed with Opti-MEM (Invitrogen, 200 μl), then TXNIP or control siRNA (60 ng) was added to the solution, mixed gently, and incubated at room temperature for 20 min. This mixture was added to HUVEC in normal culture media (2 ml) and cells were incubated for 1.5 h. The medium was changed and cells recovered for 24 h. The transfection was repeated and after 24 h, cells were used for experiments.

Bovine aortic EC ("BAEC") were purchased from Clonetics and were cultured in Medium 199 supplemented with 10% FETALCLONE III (Hyclone), basal MEM vitamins, and amino acids (Invitrogen). Cells at passages 8-10 were used for experiments. BAEC at >90% confluence in 35-mm dishes were used for transfection. For each dish, Lipofectamine 2000 (5 μl) was mixed with Opti-MEM (250 μl), then pcDNA3.1-TXNIP (Wang et al., "Vitamin D(3)-Up-Regulated Protein-1 is a Stress-Responsive Gene That Regulates Cardiomyocyte Viability Through Interaction with Thioredoxin," *J Biol Chem* 277:26496-26500 (2002); Schulze et al., "Vitamin D3-Upregulated Protein-1 (VDUP-1) Regulates Redox-Dependent Vascular Smooth Muscle Cell Proliferation Through Interaction With Thioredoxin," *Circ Res* 91:689-695 (2002), each of which is hereby incorporated by reference in its entirety) or pcDNA3.1 (2 μg) was added to the solution, mixed gently, and incubated at room temperature for 20 min. This mixture was added to BAEC in Opti-MEM (2 ml) and cells were incubated for 3 h. The medium was changed and cells recovered for 24 h. Cells were used for experiments after 18-24 h serum-starvation.

For short-term exposure to flow, cells were cultured in 60 mm dishes and placed in a cone and plate viscometer as described (Surapisitchat et al., "Fluid Shear Stress Inhibits TNF-Alpha Activation of JNK but not ERK½ or p38 in Human Umbilical Vein Endothelial Cells: Inhibitory Crosstalk Among MAPK Family Members," *Proc Natl Acad Sci USA* 98:6476-6481 (2001), which is hereby incorporated by reference in its entirety). For long-term exposure to flow (24 h), HUVECs in Medium 200 with LSGS were exposed to shear stress generated by a parallel-plate-type apparatus as previously described (Pi et al., "Big Mitogen-Activated Protein Kinase (BMK1)/ERK5 Protects Endothelial Cells From Apoptosis," *Circ Res* 94:362-369 (2004), which is hereby incorporated by reference in its entirety). Briefly, one side of the flow chamber had HUVECs growing to monolayers. The other side was a polycarbonate plate, and the two surfaces were held 200 μm apart by a GlycoTech gasket. A closed circulation was arranged with a silicone tube and an air bag filled with medium to stabilize the flow. Medium was constantly circulated with a roller/tube pump at 37° C. in 95% room air and 5% $CO_2$. Shear stress was calculated by the formula 6 $\mu Q/a^2 b$, where μ is the viscosity of the perfusate (poise), Q is flow volume (ml/s), and a and b are cross section dimensions of the flow path (cm).

Perfusion Organ Culture:

Animal experiments were performed according to the guidelines of the NIH and American Heart Association for the Care and *Use of Laboratory Animals* and were approved by the University of Rochester Animal Care Committee. Male New Zealand White rabbits (2-3 kg; Covance Research Products) were anesthetized with ketamine (50 mg/kg, i.v.) and xylazine (2 mg/kg, i.v.). Arterial segments from the descending thoracic aorta were isolated and cannulated at a constant pressure (80 mm Hg) (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003); Bardy et al., "Differential Effects of Pressure and Flow on DNA and Protein Synthesis and on Fibronectin Expression by Arteries in a Novel Organ Culture System," *Circ Res* 77:684-694 (1995); Lehoux et al., "Pulsatile Stretch-Induced Extracellular Signal-Regulated Kinase ½ Activation in Organ Culture of Rabbit Aorta Involves Reactive Oxygen Species," *Arterioscler Thromb Vasc Biol* 20:2366-2372 (2000), each of which is hereby incorporated by reference in its entirety). Isolated aortic segments were connected to a closed perfusion circuit consisting of a 3-port reservoir, a peristaltic pump, and a pressure chamber. Vessel segments were placed in a bath filled with culture medium identical to that used in the intraluminal compartment, consisting of serum-free DMEM containing antibiotics. To obtain a physiological fluid viscosity (0.04 poise), 5% Dextran (Sigma) was added. Previous reports found that this organ culture method preserved~100% EC and smooth muscle viability (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003); Bardy et al., "Differential Effects of Pressure and Flow on DNA and Protein Synthesis and on Fibronectin Expression by Arteries in a Novel Organ Culture System," *Circ Res* 77:684-694 (1995); Lehoux et al., "Pulsatile Stretch-Induced Extracellular Signal-Regulated Kinase ½ Activation in Organ Culture of Rabbit Aorta Involves Reactive Oxygen Species," *Arterioscler Thromb Vasc Biol* 20:2366-2372 (2000), each of which is hereby incorporated by reference in its entirety). Flow rate was adjusted to 7.5 mL/min for low flow and 220 mL/min for normal flow, respectively. In conditions of steady laminar flow, shear stress (σ) is determined by flow rate (Q), fluid viscosity μ, and vessel diameter (d) according to the relationship: $\sigma 32 \mu Q/\pi d^3$ Based on this calculation, shear stress was 0.4 $dyn/cm^2$ for low flow and 12 $dyn/cm^2$ for normal flow. Organ culture of the aortic segments was carried out under sterile conditions in an incubator containing 5% $CO_2$ at 37.5° C. for 24 h.

Immunoprecipitation (I.P.) and Immunoblotting (I.B):

I.P. and I.B. experiments were performed as described previously (Surapisitchat et al., "Fluid Shear Stress Inhibits TNF-Alpha Activation of JNK but not ERK½ or p38 in Human Umbilical Vein Endothelial Cells: Inhibitory Crosstalk Among MAPK Family Members," *Proc Natl Acad Sci USA* 98:6476-6481 (2001); Liu et al., "Laminar Flow Inhibits TNF-Induced ASK1 Activation by Preventing Dissociation of ASK1 From its Inhibitor 14-3-3," *J Clin Invest* 107:917-923 (2001); Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003), each of which is hereby incorporated by reference in its entirety). The resulting autoradiograms were analyzed with NIH Image 1.60. Experiments were performed at least three times and equal loading of protein was ensured by measuring actin expression.

TRX Activity (Insulin Reducing) Assay:

TRX activity was measured using the insulin disulfide reduction assay as described elsewhere with a slight modification (Junn et al., "Vitamin D3 Up-Regulated Protein 1 Mediates Oxidative Stress via Suppressing the Thioredoxin Function," *J Immunol* 164:6287-6295 (2000); Wang et al., "Vitamin D(3)-Up-Regulated Protein-1 is a Stress-Responsive Gene That Regulates Cardiomyocyte Viability Through Interaction with Thioredoxin," *J Biol Chem* 277:26496-26500 (2002), each of which is hereby incorporated by reference in its entirety). Cell extracts (10 μg, 34 μl) were incubated at 37° C. for 20 min with 1 μl of reducing buffer composed of 50 mM HEPES (pH 7.6), 1 mM EDTA, 1 mg/ml BSA, and 2 mM DTT. Then 20 μl of reaction buffer containing 200 μl of 1 M HEPES (pH 7.6), 16 μl of 0.5 M EDTA, 80 μl of NADPH (20 mg/ml), and 500 μl of insulin (10 mg/ml) was added. The reaction was started by the addition of 5 μl of bovine TRX reductase (American Diagnostica, Inc.) and continued for 20 min. at 37° C. The reaction was terminated by adding 125 μl of 10 M guanidine-HCl and 1.7 mM DTNB (3-carboxy-4-nitrophenyl disulfide), and the absorbance at 405 nm was measured spectroscopically.

TXNIP Deficient Mouse:

HcB-19 mice derived from the colony at the University of California, Los Angeles (Bodnar et al., "Positional Cloning of the Combined Hyperlipidemia Gene Hyplip 1," *Nat Genet* 30:110-116 (2002); Castellani et al., "Mapping a Gene for Combined Hyperlipidaemia in a Mutant Mouse Strain," *Nat Genet* 18:374-377 (1998), each of which is hereby incorporated by reference in its entirety) were sacrificed immediately after delivery and aortas were harvested. Animal experiments were performed according to the guidelines of the NIH and American Heart Association for the *Care and Use of Laboratory Animals* and were approved by the University of Rochester Animal Care Committee. The HcB-19 mouse is a variant of the C3H strain that was first described as a model of human familial combined hyperlipidemia (Castellani et al., "Mapping a Gene for Combined Hyperlipidaemia in a Mutant Mouse Strain," *Nat Genet* 18:374-377 (1998), which is hereby incorporated by reference in its entirety). For the present study, age-matched (8 month) and strain-matched C3H/HeJ mice were used as controls. While the C3H/HeJ control is not genetically 100% identical to the HcB-19 mice, these substrains are very similar. It is possible, though unlikely, that subtle strain differences in TNF- and flow-mediated responses might alter the results shown here. Proteins were obtained by homogenizing aortas with Triton-X lysis buffer after treatment with TNF-α for 6 h at 37° C. (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003), which is hereby incorporated by reference in its entirety).

Statistical Analysis:

Data are shown as mean±SEM. Statistical evaluation was done by unpaired Student's t test and P<0.05 was taken as a significant difference.

Example 1

Chronic Flow Down-Regulated TXNIP Expression in Rabbit Aorta Endothelial Cells

To examine the effects of chronic flow on TXNIP expression, rabbit aortas were exposed to low (0.4 dyn/cm$^2$) or normal (12 dyn/cm$^2$) fluid shear stress for 24 h. EC and vascular smooth muscle cell (VSMC) proteins were selectively purified from intact rabbit aorta as described previously (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003), which is hereby incorporated by reference in its entirety). TXNIP expression in EC was significantly inhibited by exposure to normal flow compared to low flow (64±17% inhibition, FIGS. 1A, 1C, P<0.01, n=5). Flow did not change TXNIP expression in VSMC (FIG. 1B, n=4).

Example 2

Figure 2:
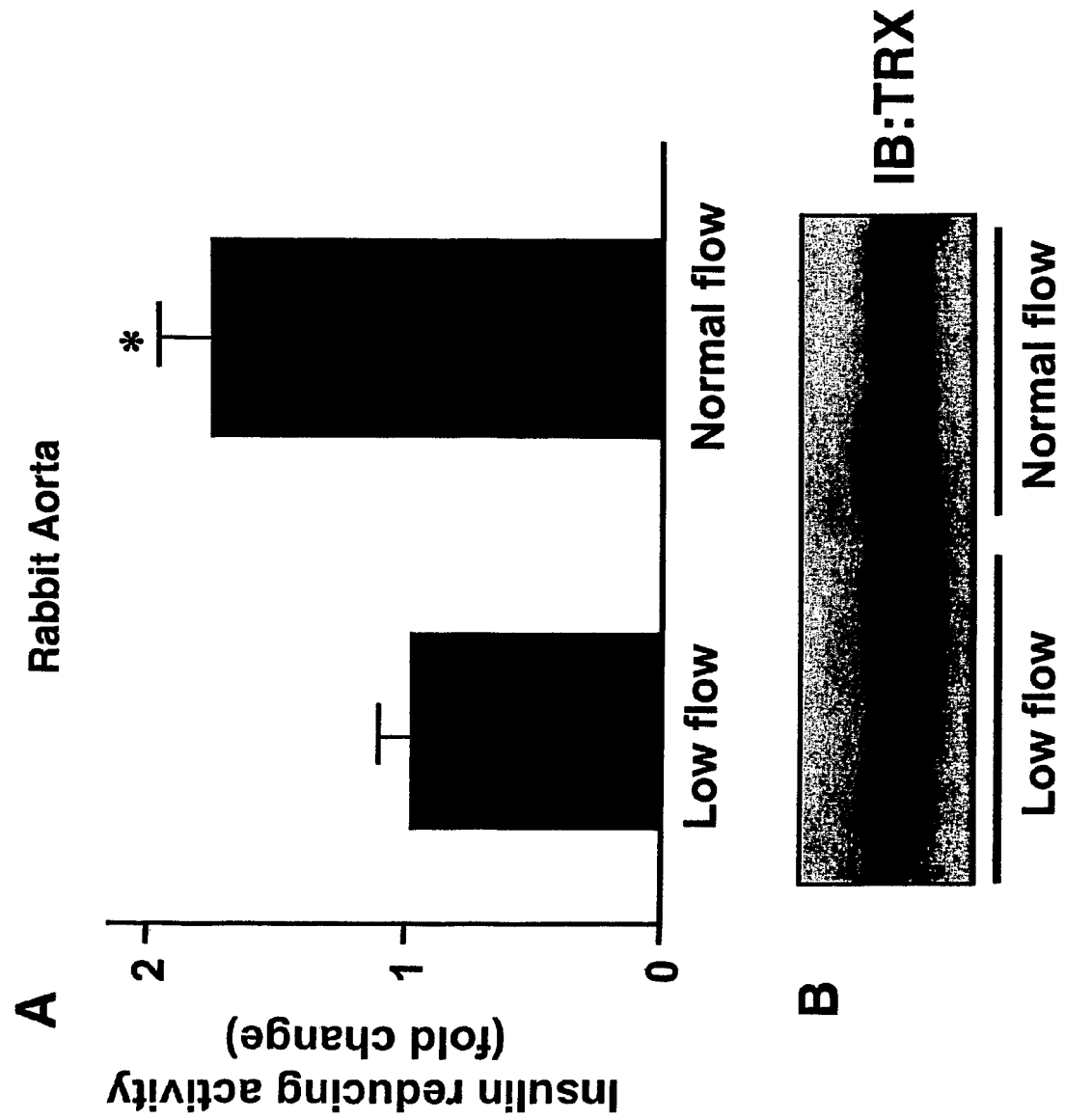
FIGS. 2A-B illustrate that normal flow increased the activity but not expression of thioredoxin (TRX) in EC. After rabbit aortas were exposed to low flow (0.4 dyn/cm$^2$) or normal flow (12 dyn/cm$^2$) for 24 h, EC lysates were harvested.

Chronic Flow Increased TRX Activity but not Expression in Rabbit Aorta Endothelial Cells The effect of flow on TRX activity was next examined. TRX binds to TXNIP and is inhibited by TXNIP (Nishiyama et al., "Identification of Thioredoxin-Binding Protein-2/Vitamin D(3) Up-Regulated Protein 1 as a Negative Regulator of Thioredoxin Function and Expression," *J Biol Chem* 274: 21645-21650 (1999); Junn et al., "Vitamin D3 Up-Regulated Protein 1 Mediates Oxidative Stress via Suppressing the Thioredoxin Function," *J Immunol* 164:6287-6295 (2000), each of which is hereby incorporated by reference in its entirety). Exposure to normal flow for 24 h significantly enhanced the insulin-reducing activity of TRX compared to low flow in EC (77±22% increase, FIG. 2A, P<0.05, n=4). Expression of TRX protein in EC did not change after flow (FIG. 2B, n=5).

Example 3

Figure 3:
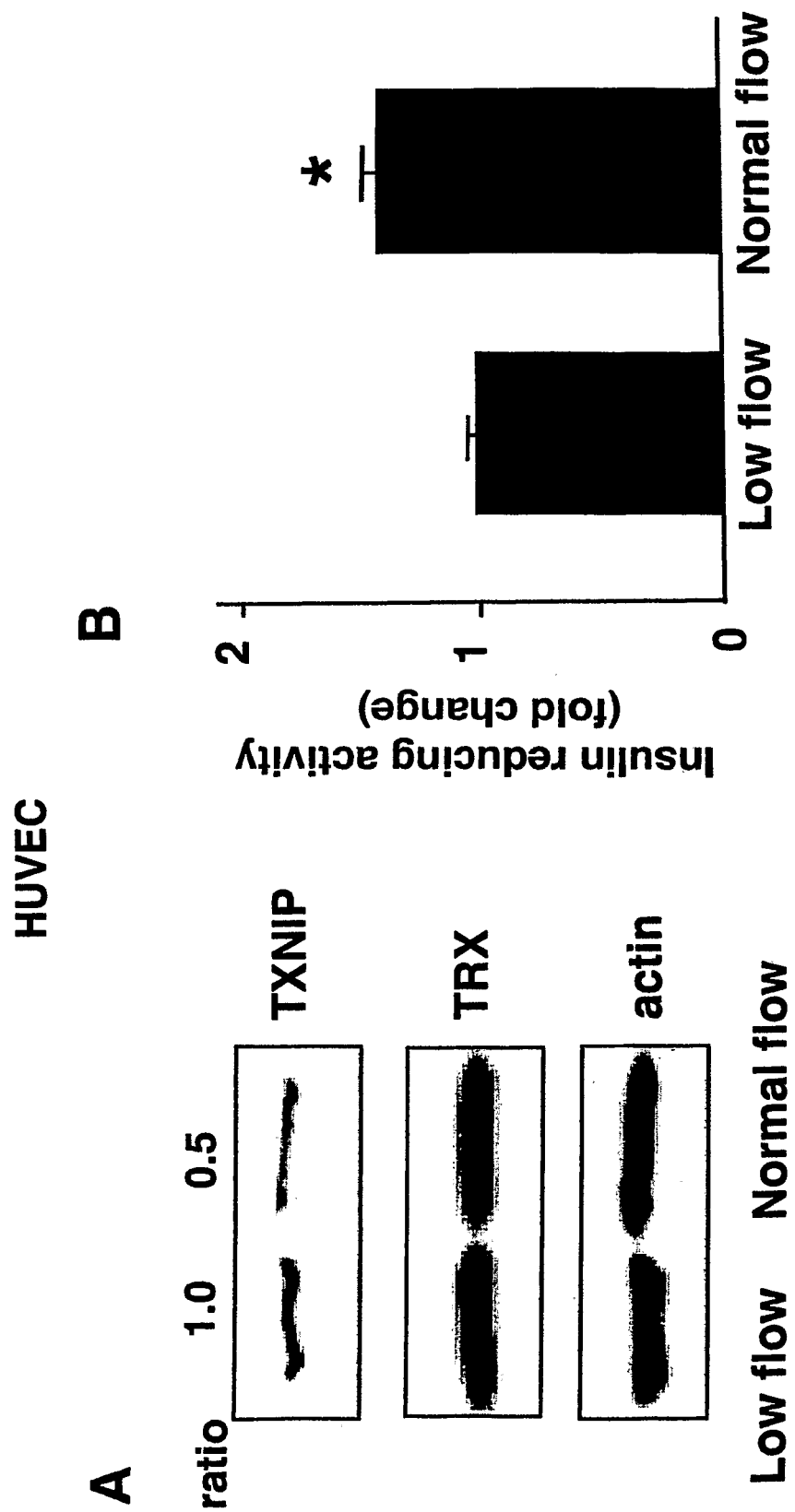
FIGS. 3A-B illustrate that normal flow down-regulated TXNIP expression and up-regulated TRX activity in human umbilical vein EC ("HUVEC"). After HUVECs were exposed to low flow (0.4 dyn/cm$^2$) or normal flow (12 dyn/cm$^2$) for 24 h, proteins were harvested.

Chronic Flow Down-Regulated TXNIP Expression and Up-Regulated TRX Activity in HUVEC In HUVEC, exposure to normal flow (fluid shear stress=12 dyn/cm2) for 24 h decreased TXNIP expression compared to low flow (0.4 dyn/cm2) (50±15% inhibition, FIG. 3A, P<0.05, n=4). While flow did not change TRX expression in HUVEC (FIG. 3A, n=4), normal flow (12 dyn/cm2 24 h) increased TRX activity (40±8% increase, FIG. 3B, P<0.05, n=4), confirming the above-identified findings in rabbit aorta.

Example 4

TXNIP siRNA Inhibited TNF Activation of p38, JNK, and VCAM1 Expression in HUVEC

It has been reported previously that exposure to normal flow for 24 h significantly inhibited TNF-stimulated JNK and p38 activity (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003), which is hereby incorporated by reference in its entirety). TNF-induced VCAM1 expression in EC was also significantly inhibited by exposure to normal flow (78% inhibition) (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003), which is hereby incorporated by reference in its entirety). It was therefore expected that normal flow prevents TNF-induced VCAM1 expression by regulating TXNIP/TRX/JNK/p38 pathways. It was previously shown that JNK and p38 mediated TNF-induced VCAM1 expression in rabbit aortic EC, and it is known that TRX inhibits the ASK1-JNK-p38 signaling pathway (Saitoh et al., "Mammalian Thioredoxin is a Direct Inhibitor of Apoptosis Signal-Regulating Kinase (ASK) 1," *EMBO J* 17:2596-2606 (1998), which is hereby incorporated by reference in its entirety).

Figure 4:
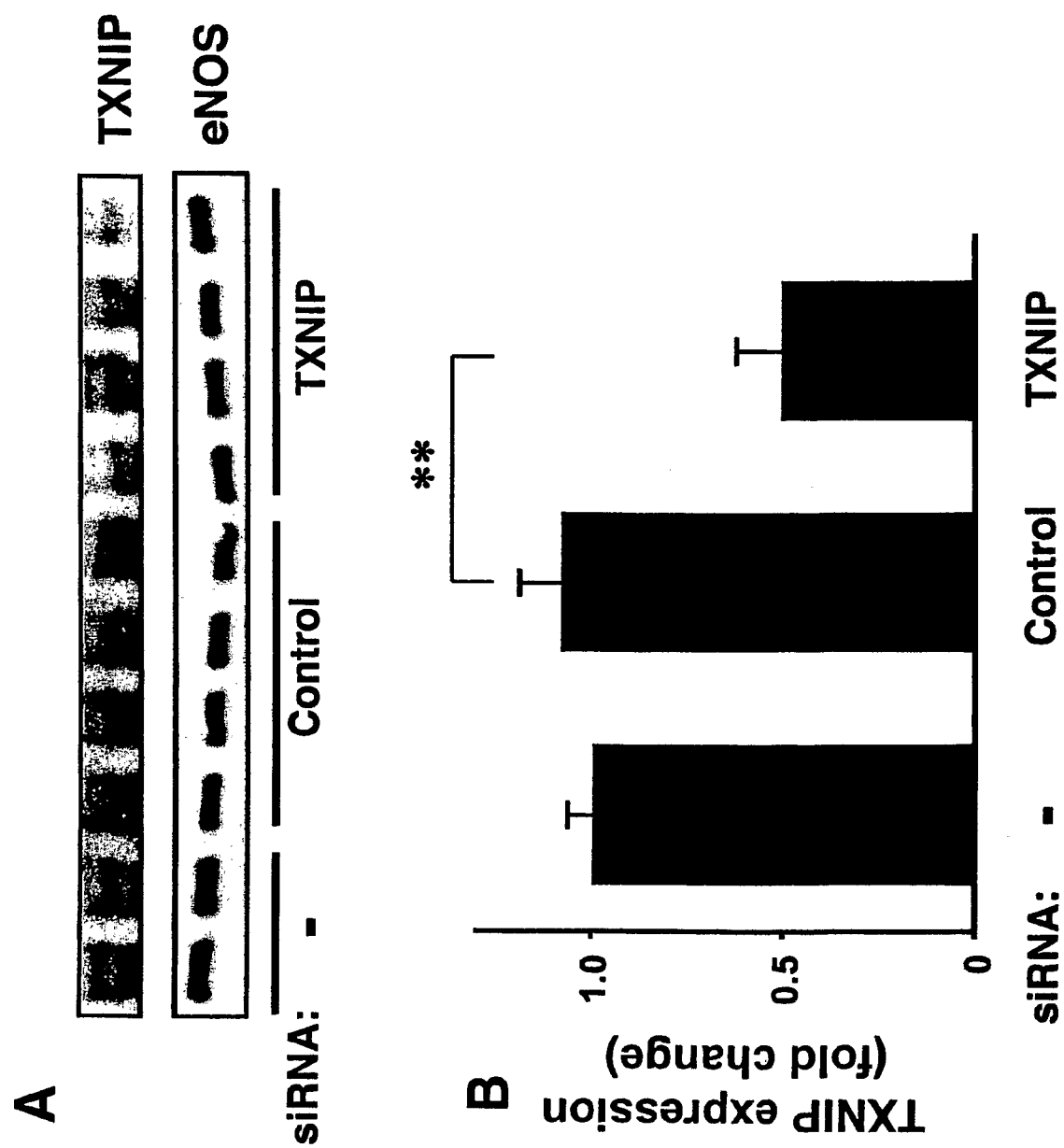
FIGS. 4A-B illustrate that TXNIP protein expression is decreased by siRNA in HUVEC. HUVEC were transfected with either control or TXNIP siRNA.
Figure 5:
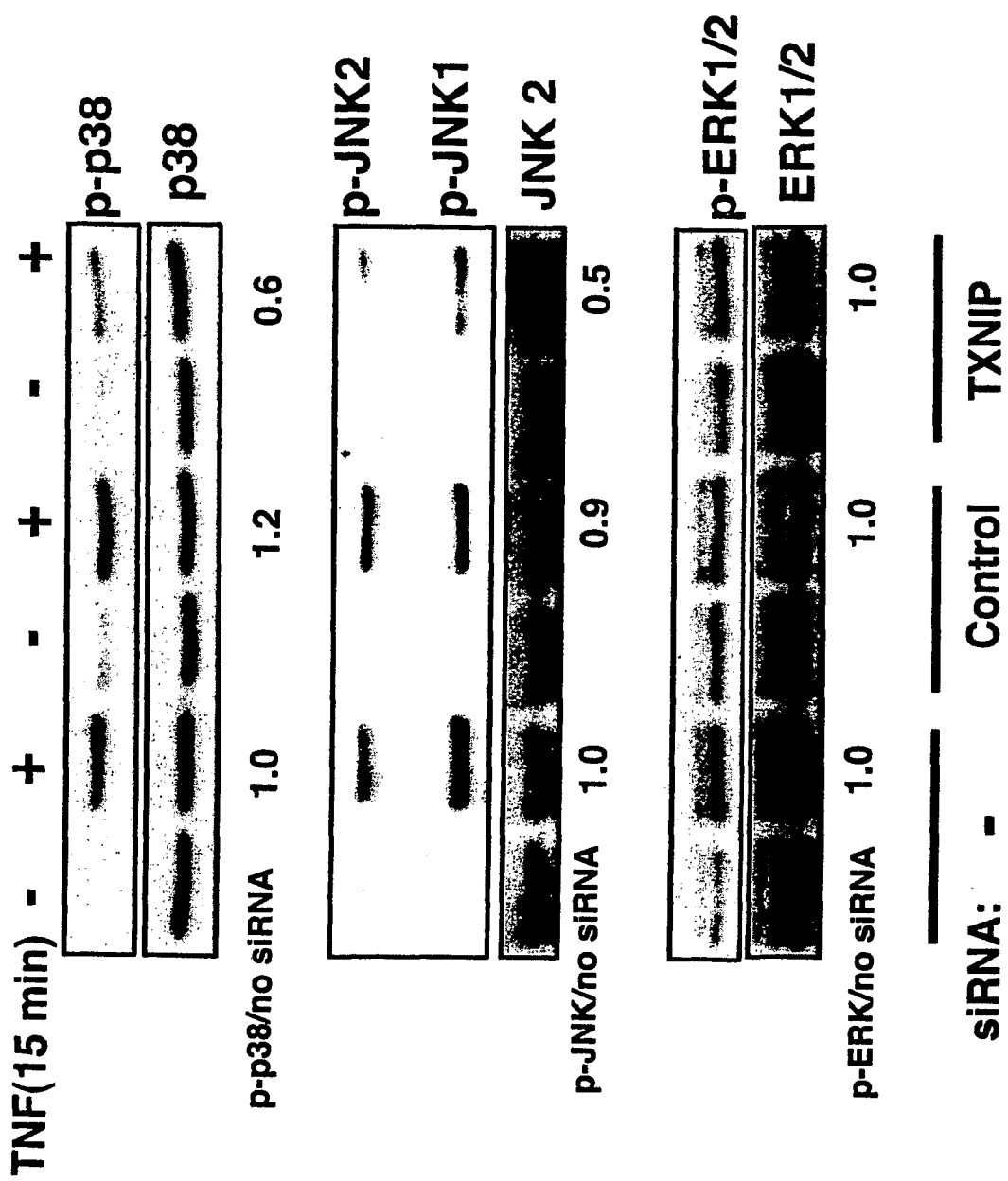
FIG. 5 illustrates that TXNIP siRNA inhibited TNF activation of p38 and JNK, but not ERK½ in HUVEC. After HUVEC were transfected with either control or TXNIP siRNA, TNF (10 ng/mL) was added for 15 min. MAP kinase activation was determined by immunoblotting using phospho-specific antibody. Equal loading was confirmed with total MAP kinase antibodies. Representative blots from three independent experiments are shown. Quantitation of the ratio of phospho-MAPK in lysates from control and TXNIP siRNA treated cells to no siRNA cells is shown below each panel (average of 3 determinations).
Figure 6:
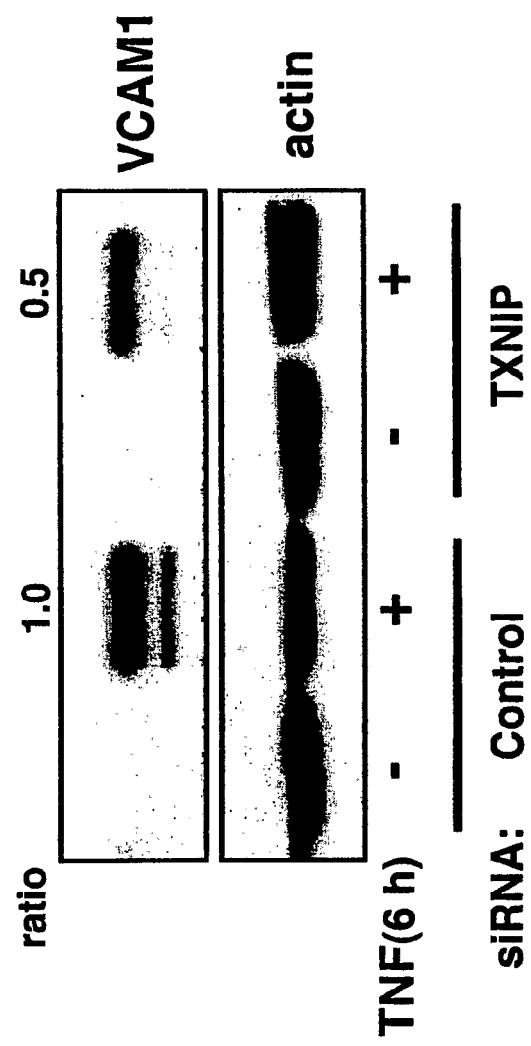
FIG. 6 illustrates that TXNIP siRNA inhibited TNF-induced VCAM1 expression in HUVEC. After HUVEC were transfected with either control or TXNIP siRNA, TNF-α (10 ng/mL) was added for 6 h. VCAM-1 expression was determined by immunoblotting from 3 independent experiments. Equal protein loading was confirmed with actin antibody. Analysis shows VCAM1 expression as fold change relative to control siRNA.

To show that inhibition of TXNIP contributes to the anti-inflammatory effects of normal flow, HUVEC were treated with siRNA against human TXNIP. TXNIP siRNA significantly decreased endogenous TXNIP protein expression (53±11% decrease) compared to control siRNA without significant effect on eNOS (FIG. 4, P<0.01, n=6). TXNIP siRNA significantly inhibited TNF (10 ng/mL, 15 min) activation of p38 (48±12% inhibition) and JNK (42±10% inhibition) compared to control siRNA (FIG. 5, P<0.05, n=3). In contrast, TNF activation of ERK½ (FIG. 5, n=3) and NF-κB (measured by IκB-A degradation, n=2) was not inhibited, suggesting a specific role for TXNIP in TNF-mediated signal events related to p38 and JNK. TXNIP siRNA also significantly inhibited TNF-induced (10 ng/mL, 6 h) VCAM1 expression in HUVEC (48±3% inhibition, FIG. 6, P<0.01, n=3). TNF-induced VCAM1 expression was almost completely blocked by inhibiting p38 (30 μM SB203580, n=4) but not ERK½ (30 μM PD98059, n=3). Of note, the JNK inhibitor (10 μM SP600125, n=4) had no effect on VCAM1 expression in HUVEC, unlike previous results in rabbit aorta (Yamawaki et al., "Chronic Physiological Shear Stress Inhibits Tumor Necrosis Factor-Induced Proinflammatory Responses in Rabbit Aorta Perfused ex vivo," *Circulation* 108:1619-1625 (2003), which is hereby incorporated by reference in its entirety). These data suggest that inhibiting TXNIP decreases EC inflammatory responses (measured by TNF activation of VCAM1) by preventing p38 and/or JNK activation.

Example 5

TXNIP siRNA Increased TRX Binding to ASK1 in HUVEC

Junn et al. showed that binding of TRX to ASK1 was significantly reduced when TXNIP was over-expressed (Junn et al., "Vitamin D3 Up-Regulated Protein 1 Mediates Oxidative Stress via Suppressing the Thioredoxin Function," *J Immunol* 164:6287-6295 (2000), which is hereby incorporated by reference in its entirety), suggesting that TXNIP can compete with TRX for binding to ASK1. Thus, the effect of decreasing TXNIP on interaction of TRX with ASK1 was examined.

Figure 7:
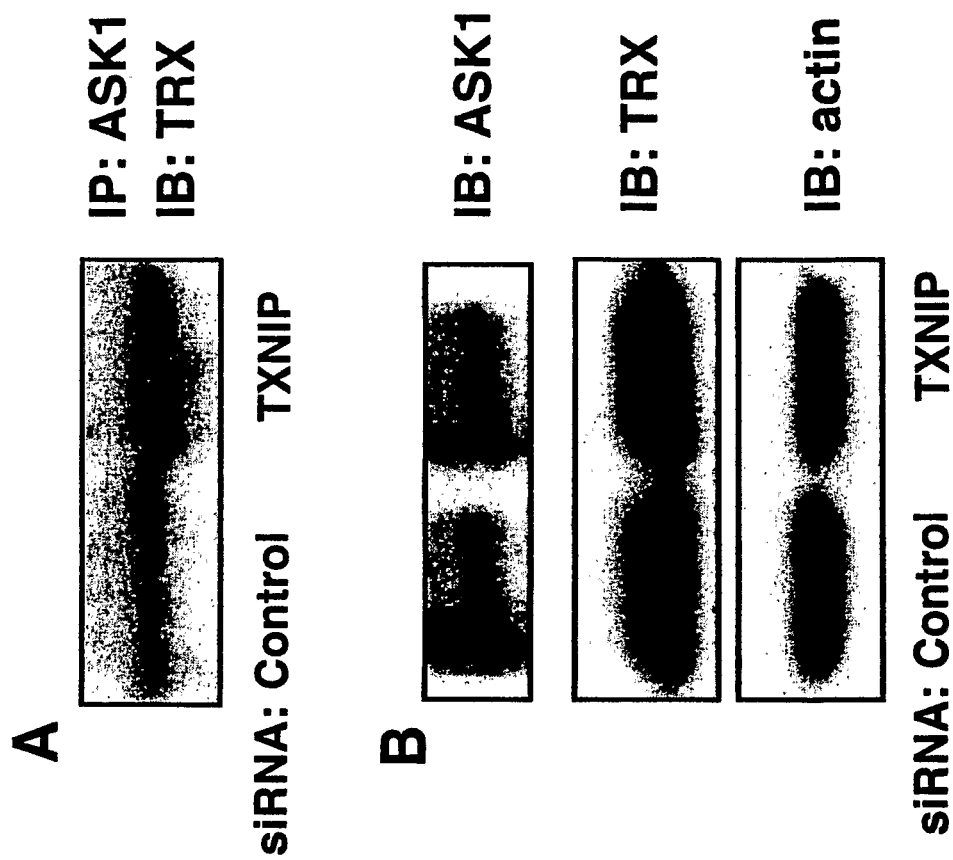
FIG. 7A-B illustrate that TXNIP siRNA increased TRX binding to ASK1 in HUVEC. Interaction of ASK1 with TRX was examined by immunoblotting (IB) with TRX antibody after HUVEC lysates were immunoprecipitated (IP) with ASK1 antibody. Equal loading was confirmed with ASK1, TRX, and actin antibodies (FIG. 7B). Results are representative of 4 independent experiments.

Treatment of HUVEC with TXNIP siRNA increased ASK1 binding to TRX (FIG. 7A, n=4). TXNIP siRNA did not change the expression of ASK1 and TRX (FIG. 7B). These results suggest that TXNIP regulates the binding of TRX to ASK1 in HUVEC.

Example 6

TXNIP Overexpression Augmented TNF Activation of p38 and JNK in BAEC

Figure 8:
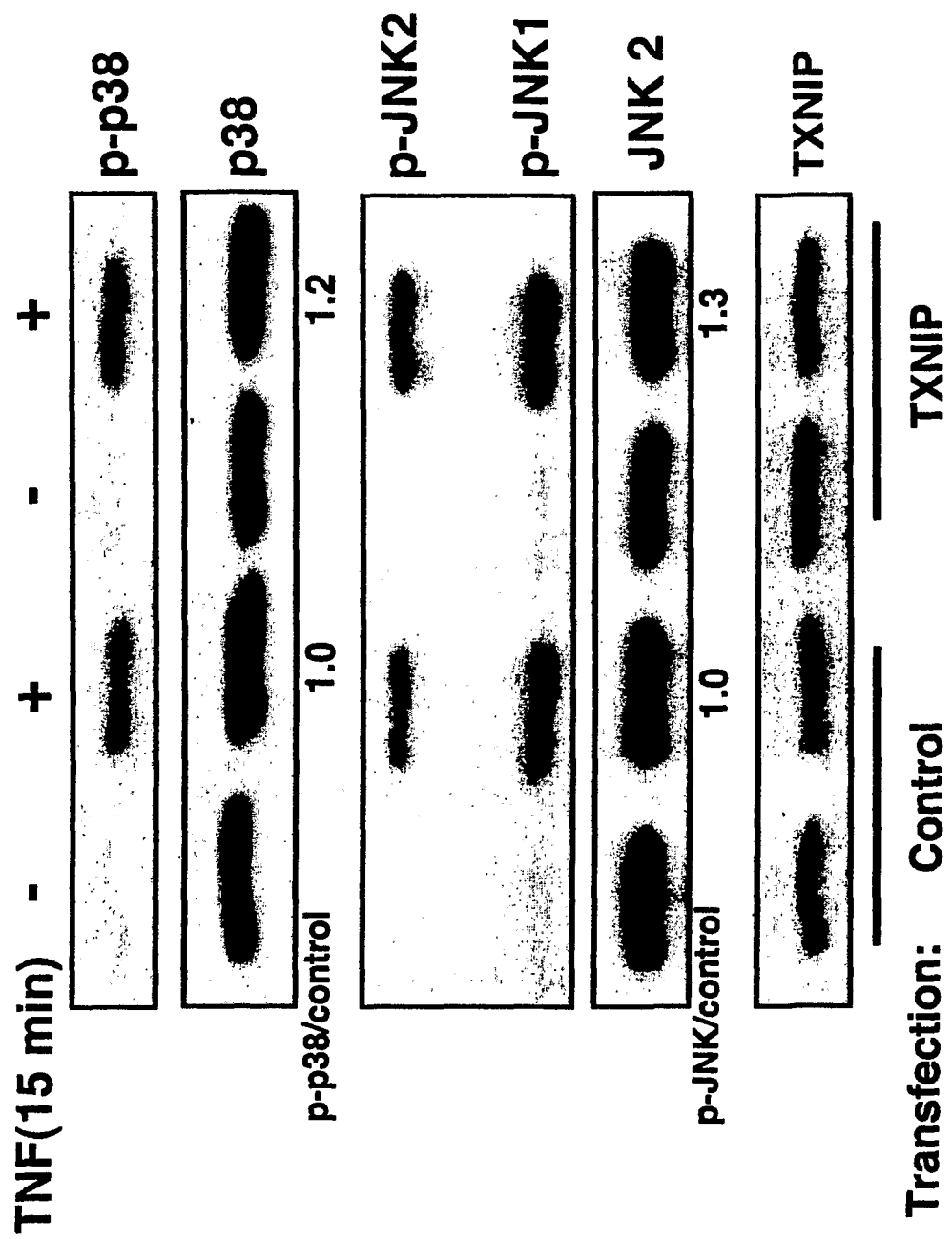
FIG. 8 illustrates that TXNIP over-expression augmented TNF-induced p38 and JNK activation in bovine aortic endothelial cells ("BAEC"). After BAEC were transfected with either control (pcDNA3.1) or pcDNA3.1-TXNIP, TNF-α (10 ng/mL) was treated for 15 min. Activation of p38 and JNK was determined by immunoblotting using phospho-specific antibody. Equal loading was confirmed with total MAP kinase antibodies. Representative blots from 3-4 independent experiments are shown.

To further examine the contribution of TXNIP to inflammatory responses in EC, TXNIP was overexpressed in BAEC. Over-expressing TXNIP significantly enhanced TNF-mediated activation of p38 (23±7% increase, FIG. 8, n=3; P<0.05) and JNK (33±11% increase, FIG. 8, n=4; P<0.05) indicating an important role for TXNIP-TRX interactions in regulating p38 and JNK in EC.

Example 7

TNF-Induced VCAM1 Expression is Decreased in TXNIP Deficient Mouse

Figure 9:
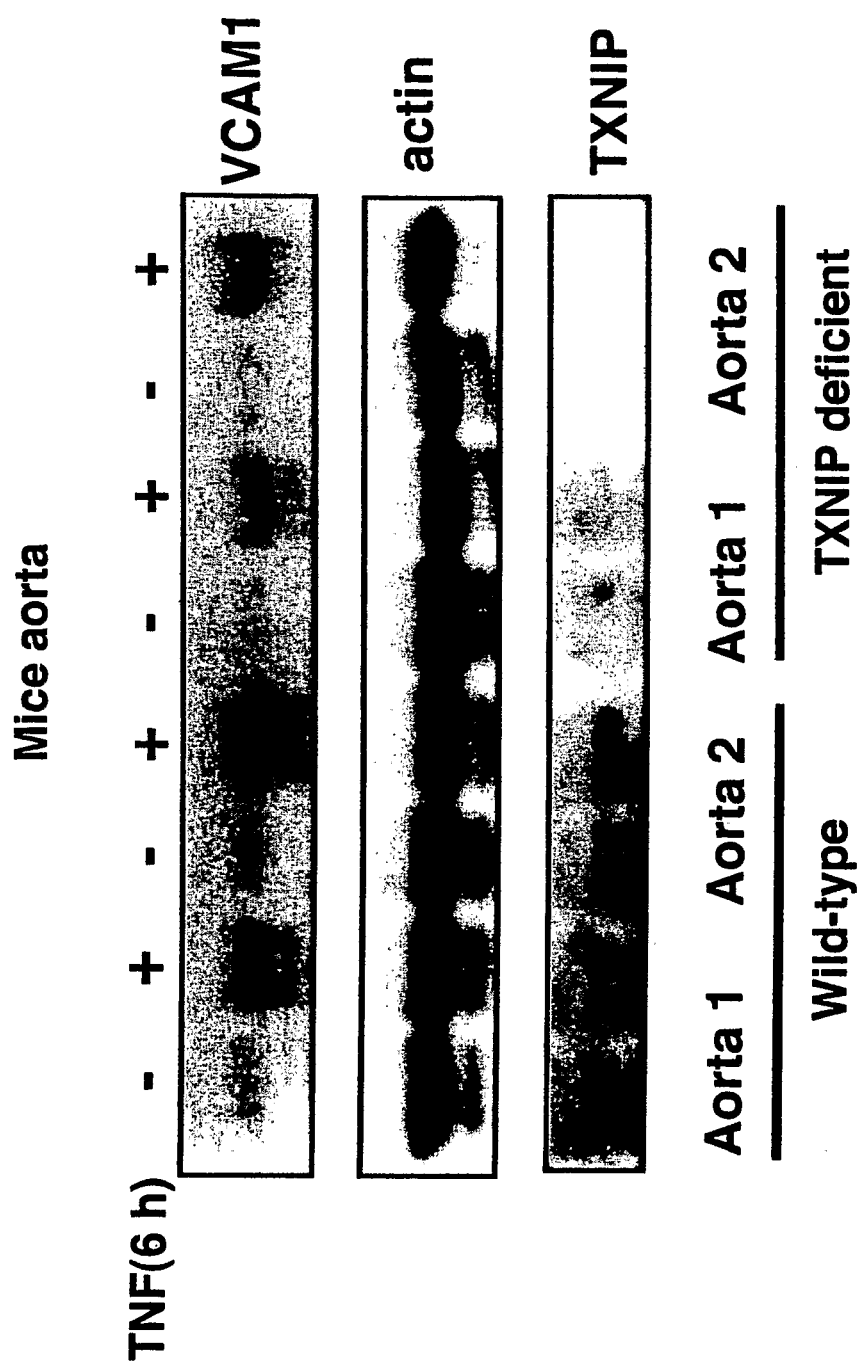
FIG. 9 illustrates that TNF-induced VCAM1 expression is decreased in TXNIP-deficient mouse aorta. After aortas from HcB-19 and control C3H mice were treated with TNF (15 ng/mL, 6 h), vessel protein was harvested. Expression of VCAM1 and TXNIP was determined by immunoblotting in two aortic samples from 2 animals of each strain. Equal protein loading was confirmed with actin antibody.

The role of TXNIP in inflammatory responses was examined in vivo. Recently, an animal model of combined hyperlipidemia (the HcB-19/Deni mouse) including hypertriglyceridemia, hypercholesterolemia, elevated plasma apolipoprotein B, and increased triglyceride-rich lipoproteins, was shown to have a nonsense mutation in TXNIP resulting in very low protein expression (Bodnar et al., "Positional Cloning of the Combined Hyperlipidemia Gene Hyplip 1," *Nat Genet* 30:110-116 (2002), which is hereby incorporated by reference in its entirety). It appears that the hyperlipidemia results from excess triglyceride and cholesterol synthesis by the liver rather than impaired EC function. Aortas from HcB-19 mice had nearly undetectable TXNIP compared to C3H mice (FIG. 9, n=2), confirming the previously published data showing decreased TXNIP mRNA expression (Bodnar et al., "Positional Cloning of the Combined Hyperlipidemia Gene Hyplip 1," *Nat Genet* 30:110-116 (2002), which is hereby incorporated by reference in its entirety). In HcB-19 aorta, TNF-induced (15 ng/mL, 6 h) VCAM1 expression was suppressed (51% decrease, FIG. 9, n=2). It appears that even under resting conditions VCAM1 expression in HcB-19 aorta is less than in wild type aorta. These results support the hypothesis that inhibiting TXNIP expression contributes to the anti-inflammatory effects of flow in EC.

Discussion of Examples 1-7

Figure 10:
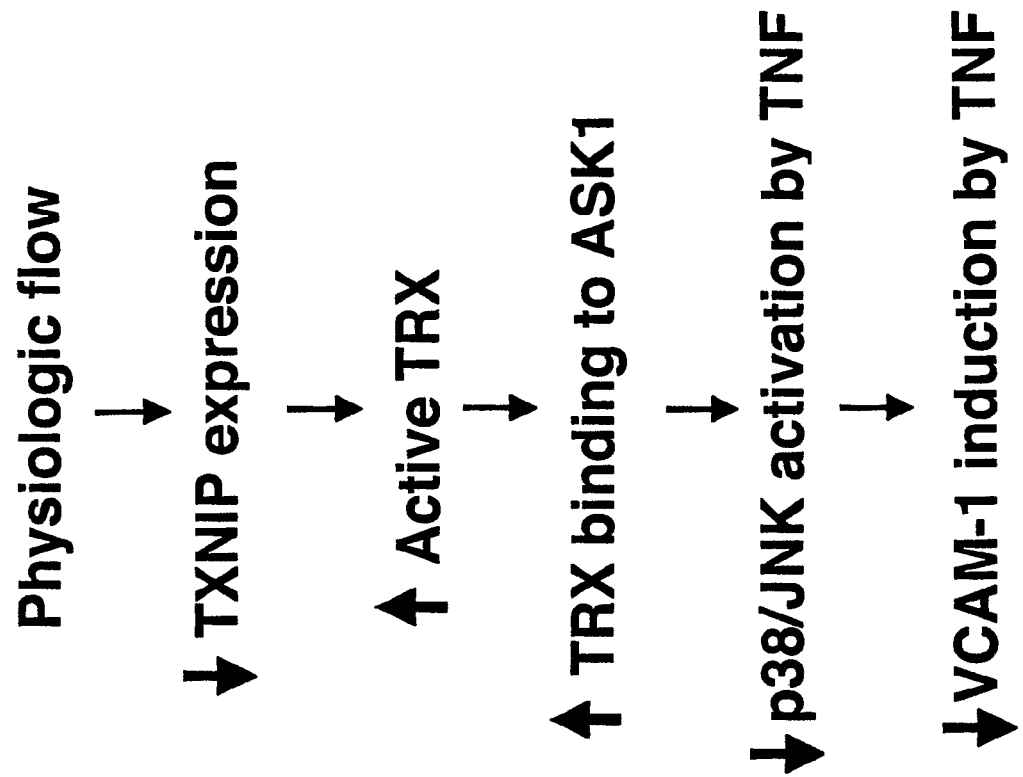
FIG. 10 is a diagram that illustrates the relationship between flow-regulated TXNIP expression in EC and inhibition of pro-inflammatory events. Chronic exposure to normal flow decreased TXNIP expression, which results in increased TRX binding to ASK1. This inhibits cytokine (e.g., TNF) activation of JNK-p38 pathway and prevents pro-inflammatory events such as VCAM1 expression.

The major findings of the present study are that physiologic fluid shear stress decreases TXNIP expression and limits pro-inflammatory events mediated by the TNF-ASK1-JNK-p38 pathway (FIG. 10). It intact aortas it was found that physiologic flow decreased TXNIP expression, and decreased TXNIP expression was associated with decreased TNF-mediated VCAM1 expression. The results are the first demonstration of the physiologic function of TXNIP in vascular endothelium. The data support the evolving concept that TXNIP-TRX are key components of biomechanical signal transduction and establish TXNIP-TRX as novel regulators of TNF signaling and inflammation in the endothelium.

Several results suggest that TXNIP is a critical target for the anti-inflammatory effects of steady laminar flow. TXNIP was shown to inhibit the catalytic activity of TRX (Nishiyama et al., "Identification of Thioredoxin-Binding Protein-2/Vitamin D(3) Up-Regulated Protein 1 as a Negative Regulator of Thioredoxin Function and Expression," *J Biol Chem* 274: 21645-21650 (1999); Junn et al., "Vitamin D3 Up-Regulated Protein 1 Mediates Oxidative Stress via Suppressing the Thioredoxin Function," *J Immunol* 164:6287-6295 (2000), each of which is hereby incorporated by reference in its entirety). This is important because only catalytically active (or reduced) TRX can bind to ASK1 and inhibit ASK1-dependent JNK and p38 activity (Saitoh et al., "Mammalian Thioredoxin is a Direct Inhibitor of Apoptosis Signal-Regulating Kinase (ASK) 1," *EMBO J* 17:2596-2606 (1998), which is hereby incorporated by reference in its entirety).

The results in the preceding examples show that chronic normal flow increased the catalytic activity of TRX (as measured by insulin reduction) in arterial EC, confirming data in cultured EC (Hoffmann et al., "Shear Stress Increases the Amount of S-Nitrosylated Molecules in Endothelial Cells: Important Role for Signal Transduction," *FEBS Lett* 551:153-158 (2003), which is hereby incorporated by reference in its entirety). Thus, it is suggested that flow inhibition of TXNIP expression makes more reduced TRX available to bind to ASK1 and inhibits JNK and p38 activation. It was previously shown in cultured EC that steady laminar flow of short duration (10 min.) inhibited TNF activation of ASK1-JNK pathways by increasing ASK1 association with its inhibitor 14-3-3 but not TRX (Liu et al., "Laminar Flow Inhibits TNF-Induced ASK1 Activation by Preventing Dissociation of ASK1 From its Inhibitor 14-3-3," *J Clin Invest* 107:917-923 (2001), which is hereby incorporated by reference in its entirety), suggesting that there are differences in regulation of ASK1 between acute and chronic flow. Another important mechanism by which flow inhibits inflammation is by inducing a reduced intracellular redox state since flow maintains the key antioxidant molecules TRX and glutaredoxin (Song et al., "Role of Glutaredoxin in Metabolic Oxidative Stress. Glutaredoxin as a Sensor of Oxidative Stress Mediated by $H_2O_2$," *J Biol Chem* 277:46566-46575 (2002), which is hereby incorporated by reference in its entirety) in their reduced forms, which bind and inhibit ASK1. It was previously shown in cultured EC that steady laminar flow inhibited H2O2-mediated activation of JNK by inducing a reduced intracellular redox state as measured by the level of reduced glutathione (Hojo et al., "Fluid Shear Stress Attenuates Hydrogen Peroxide-Induced c-Jun NH2-Terminal Kinase Activation via a Glutathione Reductase-Mediated Mechanism," *Circ Res* 91:712-718 (2002), which is hereby incorporated by reference in its entirety). Thus, it seems likely that steady laminar flow limits EC inflammation by multiple regulatory mechanisms.

TXNIP was originally identified in HL-60 leukemia cells treated with 1,25-dihydroxyvitamin D3 (Chen et al., "Isolation and Characterization of a Novel cDNA from HL-60 Cells Treated with 1,25-Dihydroxyvitamin D-3," *Biochim Biophys Acta* 1219:26-32 (1994), which is hereby incorporated by reference in its entirety). It was also shown that TGF-β1induced TXNIP in SNU-16/620 human stomach cancer cells (Han et al., "VDUP 1 Upregulated by TGF-Beta 1 and 1,25-Dihydroxyvitamin D3 Inhibits Tumor Cell Growth by Blocking Cell-Cycle Progression," *Oncogene* 22:4035-4046 (2003), which is hereby incorporated by reference in its entirety). However, the stimuli that regulate TXNIP in cardiovascular tissues remain poorly defined. Wang et al. recently demonstrated in cardiomyocytes that biomechanical strain suppressed TXNIP expression followed by increases in TRX activity (Wang et al., "Vitamin D(3)-Up-Regulated Protein-1 is a Stress-Responsive Gene That Regulates Cardiomyocyte Viability Through Interaction with Thioredoxin," *J Biol Chem* 277:26496-26500 (2002), which is hereby incorporated by reference in its entirety). Overexpression of TXNIP sensitized cells to $H_2O_2$-induced apoptosis, whereas overexpression of TRX protected against injury (Wang et al., "Vitamin D(3)-Up-Regulated Protein-1 is a Stress-Responsive Gene That Regulates Cardiomyocyte Viability Through Interaction with Thioredoxin," *J Biol Chem* 277:26496-26500 (2002), which is hereby incorporated by reference in its entirety). It was also demonstrated that PDGF suppressed TXNIP expression with increases in TRX activity and DNA synthesis in VSMC (Schulze et al., "Vitamin D3-Upregulated Protein-1 (VDUP-1) Regulates Redox-Dependent Vascular Smooth Muscle Cell Proliferation Through Interaction With Thioredoxin," *Circ Res* 91:689-695 (2002), which is hereby incorporated by reference in its entirety). Conversely, overexpression of TXNIP abolished PDGF-induced TRX activity and DNA synthesis. These results suggest that TXNIP has pro-apoptotic effects in cardiomyocytes and VSMC through the suppression of TRX activity. In the preceding examples, it was found in EC that steady laminar flow decreased TXNIP expression and limited inflammation mediated by the TNF-ASK1-JNK-p38 pathways. Since inflammation and apoptosis are key mechanisms in atherosclerosis, TXNIP is appropriately considered a novel biomechanical effector of atherosclerosis.

Example 8

Administration of a TXNIP Inhibitor to Treat a Patient for a Vascular Disease or Condition An anti-TXNIP antibody fragment that blocks TXNIP binding to TRX will be administered intravenously in a liposomal formulation to a patient suffering from one or more of the following conditions: atherosclerosis, stroke, ischemia, myocardial infarction, coronary artery disease, cardio-vascular disease, hypertension, peripheral vascular disease, heart failure, diabetes, and sepsis. It is expected that the anti-TXNIP antibody fragment will limit inflammation mediated by the TNF-ASK1-JNK-p38 pathways, and thereby reduce symptoms associated with the one or more conditions listed above.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of treating a vascular disease characterized by reduced laminar flow in a subject comprising:
    selecting a subject having a vascular disease characterized by reduced laminar flow; and
    administering to the selected subject a therapeutically effective amount of a nucleic acid molecule that inhibits expression of thioredoxin interacting protein (TXNIP) under conditions effective to inhibit expression of TXNIP in endothelial or vascular smooth muscle cells, thereby treating the vascular disease characterized by reduced laminar flow.

2. The method according to claim 1, wherein said administering is carried out orally, by inhalation, by intranasal instillation, topically, transdermally, parenterally, subcutaneously, intravenous injection, intra-arterial injection, intramuscular injection, intrapleural instillation, intraperitoneally injection, intraventricularly, intralesionally, by application to mucous membranes, or by implantation of a sustained release vehicle.

3. The method according to claim 1, wherein said treating is effective to inhibit pro-inflammatory activity of the TNF-ASK1-JNK-p38 pathways.

4. The method according to claim 1, wherein the endothelial or vascular smooth muscle cells are associated with disease-affected vasculature.

5. The method according to claim 1, wherein the nucleic acid molecule is an inhibitory RNA molecule.

6. The method according to claim 5, wherein the inhibitory RNA molecule is an siRNA molecule.

7. The method according to claim 6, wherein the siRNA molecule is targeted to SEQ ID NO: 1.

8. A method of treating a vascular disease condition in a subject comprising:
   providing an siRNA molecule that is targeted to SEQ ID NO: 1 and inhibits expression of thioredoxin interacting protein (TXNIP); and
   administering a therapeutically effective amount of the siRNA molecule to a subject under conditions effective to inhibit expression of TXNIP in endothelial or vascular smooth muscle cells, thereby treating the vascular disease condition.

9. A method of treating a vascular disease characterized by reduced laminar flow in a subject comprising:
   selecting a subject having a vascular disease characterized by reduced laminar flow which is selected from the group consisting of atherosclerosis, coronary artery disease, cardiovascular disease, hypertension, peripheral vascular disease, diabetes, and sepsis; and
   administering to the selected subject a therapeutically effective amount of a nucleic acid molecule that inhibits expression of thioredoxin interacting protein (TXNIP) under conditions effective to inhibit expression of TXNIP in endothelial or vascular smooth muscle cells, thereby treating the vascular disease characterized by reduced laminar flow.

* * * * *